US012194303B2

United States Patent
Pronovici et al.

(10) Patent No.: US 12,194,303 B2
(45) Date of Patent: *Jan. 14, 2025

(54) MODE SWITCHING IN A VENTRICULAR PACEMAKER TO PROMOTE ATRIOVENTRICULAR CONDUCTION

(71) Applicant: Medtronic, Inc., Minneapolis, MN (US)

(72) Inventors: Juliana E. Pronovici, New Hope, MN (US); James W. Busacker, St. Anthony, MN (US); Keelia M. Escalante, Minneapolis, MN (US); Vincent P. Ganion, Blaine, MN (US); Greggory R. Herr, Blaine, MN (US); Todd J. Sheldon, North Oaks, MN (US); Vincent E. Splett, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 90 days.

This patent is subject to a terminal disclaimer.

(21) Appl. No.: 17/681,678

(22) Filed: Feb. 25, 2022

(65) Prior Publication Data

US 2022/0176127 A1 Jun. 9, 2022

Related U.S. Application Data

(63) Continuation of application No. 16/702,928, filed on Dec. 4, 2019, now Pat. No. 11,260,234.

(Continued)

(51) Int. Cl.
*A61N 1/368* (2006.01)
*A61N 1/365* (2006.01)

(52) U.S. Cl.
CPC ....... *A61N 1/3688* (2013.01); *A61N 1/36542* (2013.01)

(58) Field of Classification Search
CPC .............. A61N 1/3688; A61N 1/36542; A61N 1/37205; A61N 1/3756; A61N 1/36578
See application file for complete search history.

(56) References Cited

U.S. PATENT DOCUMENTS

| 4,485,813 A | 12/1984 | Anderson et al. |
| 5,052,388 A | 10/1991 | Sivula et al. |

(Continued)

FOREIGN PATENT DOCUMENTS

| CN | 104768609 A | 7/2015 |
| CN | 105148403 A | 12/2015 |

(Continued)

OTHER PUBLICATIONS

C00019757.WO01 (PCT/US2019/064619) PCT Notification of Transmittal of the International Search Report and the Written Opinion of the International Searching Authority, dated Mar. 23, 2020, 9 pages.

(Continued)

*Primary Examiner* — Brian T Gedeon

(57) ABSTRACT

A pacemaker is configured to operate in an atrial synchronous ventricular pacing mode and, after expiration of a conduction check time interval, switch to an asynchronous ventricular pacing mode that includes setting a ventricular pacing interval to a base pacing rate interval. The pacemaker is further configured to determine when atrioventricular block detection criteria are satisfied during the asynchronous ventricular pacing mode and, responsive to the atrioventricular block detection criteria being satisfied, switch back to the atrial synchronous ventricular pacing mode.

22 Claims, 8 Drawing Sheets

Related U.S. Application Data

(60) Provisional application No. 62/776,010, filed on Dec. 6, 2018.

(56) References Cited

U.S. PATENT DOCUMENTS

| | | | |
|---|---|---|---|
| 5,312,454 A | 5/1994 | Roline et al. |
| 5,507,782 A | 4/1996 | Kieval et al. |
| 5,507,785 A | 4/1996 | Deno |
| 5,593,431 A | 1/1997 | Sheldon |
| 5,683,432 A | 11/1997 | Goedeke et al. |
| 5,720,769 A | 2/1998 | van Oort et al. |
| 5,755,740 A | 5/1998 | Nappholz |
| 5,885,471 A | 3/1999 | Ruben et al. |
| 6,044,297 A | 3/2000 | Sheldon et al. |
| 6,772,005 B2 | 8/2004 | Casavant et al. |
| 7,565,196 B2 | 7/2009 | Sheldon et al. |
| 7,783,350 B2 | 8/2010 | Sheldon et al. |
| 7,818,059 B2 | 10/2010 | Rueter et al. |
| 7,835,788 B1 | 11/2010 | Godau et al. |
| 7,881,793 B2 | 2/2011 | Betzold et al. |
| 8,170,666 B2 | 5/2012 | Sheldon |
| 8,244,351 B2 | 8/2012 | Husby |
| 8,433,409 B2 | 4/2013 | Johnson et al. |
| 8,478,407 B2 | 7/2013 | Demmer et al. |
| 8,532,785 B1 | 9/2013 | Crutchfield et al. |
| 8,541,131 B2 | 9/2013 | Lund et al. |
| 8,755,884 B2 | 6/2014 | Demmer et al. |
| 9,042,984 B2 | 5/2015 | Demmer et al. |
| 9,126,051 B2 | 9/2015 | Seim |
| 9,233,249 B2 | 1/2016 | Rouw et al. |
| 9,375,579 B2 | 6/2016 | Casavant et al. |
| 9,399,140 B2 | 7/2016 | Cho et al. |
| 9,440,081 B2 | 9/2016 | Demmer et al. |
| 9,492,669 B2 | 11/2016 | Demmer et al. |
| 9,687,654 B2 | 6/2017 | Sheldon et al. |
| 9,724,518 B2 | 8/2017 | Sheldon et al. |
| 9,775,982 B2 | 10/2017 | Grubac et al. |
| 10,207,116 B2 | 2/2019 | Sheldon et al. |
| 10,286,214 B2 | 5/2019 | Demmer et al. |
| 10,328,270 B2 | 6/2019 | Demmer et al. |
| 10,350,417 B2 | 7/2019 | Cao et al. |
| 2005/0267538 A1 | 12/2005 | Kramer et al. |
| 2008/0009910 A1 | 1/2008 | Kretschmer et al. |
| 2008/0255628 A1 | 10/2008 | Seim |
| 2012/0221070 A1 | 8/2012 | Betzold et al. |
| 2016/0114161 A1 | 4/2016 | Amblard et al. |
| 2018/0085588 A1 | 3/2018 | Splett et al. |
| 2018/0085589 A1 | 3/2018 | Splett et al. |

FOREIGN PATENT DOCUMENTS

| | | |
|---|---|---|
| CN | 106362289 A | 2/2017 |
| CN | 107750179 A | 3/2018 |
| WO | 2010099421 A1 | 9/2010 |

OTHER PUBLICATIONS

First Office Action for CN Application No. 201980079508.6 dated Feb. 1, 2024, 13 pages.

MODE SWITCHING IN A VENTRICULAR PACEMAKER TO PROMOTE ATRIOVENTRICULAR CONDUCTION

REFERENCE TO RELATED APPLICATIONS

This application is a Continuation of U.S. patent application Ser. No. 16/702,928, filed Dec. 4, 2019, which claims the benefit of provisional U.S. Patent Application No. 62/776,010, filed on Dec. 6, 2018, both of which are incorporated herein by reference in their entirety.

TECHNICAL FIELD

This disclosure relates to a cardiac pacemaker and method for delivering ventricular pacing.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (AV) node. The AV node responds by propagating a ventricular depolarization signal through the bundle of His of the ventricular septum and thereafter to the bundle branches and the Purkinje muscle fibers of the right and left ventricles.

Patients with a conduction system abnormality, e.g., poor AV node conduction or poor SA node function, may receive a pacemaker to restore a more normal heart rhythm and AV synchrony. Ventricular pacing may be performed to maintain a ventricular rate in a patient having atrioventricular conduction abnormalities. Dual chamber pacemakers are available which include a transvenous atrial lead carrying electrodes which are placed in the right atrium and a transvenous ventricular lead carrying electrodes that are placed in the right ventricle via the right atrium. The dual chamber pacemaker senses atrial electrical signals and ventricular electrical signals from the respective atrial and ventricular heart chamber electrodes and can provide both atrial pacing and ventricular pacing as needed to promote a normal heart rhythm and AV synchrony. The pacemaker itself is generally implanted in a subcutaneous pocket with the transvenous leads tunneled to the subcutaneous pocket.

Intracardiac pacemakers are available or have been proposed that are implantable within a ventricular chamber of a patient's heart for delivering ventricular pacing pulses. The intracardiac ventricular pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some heart rhythm conditions, patients having AV block may benefit from atrial-synchronized ventricular pacing in order to maintain synchrony between the atrial and ventricular contractions and a more normal heart rhythm.

SUMMARY

The techniques of this disclosure generally relate to a pacemaker capable of delivering atrial synchronous ventricular pacing during periods of AV block and switching to asynchronous ventricular pacing during periods of AV conduction to promote AV conduction along the heart's natural conduction system and minimize ventricular pacing frequency. Atrial synchronous ventricular pacing may be delivered by sensing atrial events from an intraventricular signal produced by a sensor, such as an accelerometer. The pacemaker may be an intracardiac ventricular pacemaker including the sensor producing the intraventricular signal comprising atrial event signals. A pacemaker operating according to the techniques disclosed herein controls switching between an atrial synchronous ventricular pacing mode and an asynchronous ventricular pacing mode to check for intrinsic AV conduction. The pacemaker may remain in the asynchronous ventricular pacing mode as long as AV block is not detected. The pacemaker may switch from the atrial synchronous or asynchronous pacing mode to a rate response asynchronous pacing mode to provide ventricular rate support during periods of increased patient activity.

In one example, the disclosure provides a pacemaker including a pulse generator configured to generate pacing pulses, a cardiac electrical signal sensing circuit configured to sense R-waves attendant to depolarizations of a ventricle of a patient's heart, a sensor configured to produce an intraventricular signal comprising atrial event signals, and a control circuit in communication with the sensor, the cardiac electrical signal sensing circuit, and the pulse generator. The control circuit is configured to set a timer to a conduction check time interval and operate in an atrial synchronous ventricular pacing mode. After expiration of the conduction check time interval, the control circuit switches to an asynchronous ventricular pacing mode. The control circuit is configured to determine that AV block detection criteria are satisfied during the asynchronous ventricular pacing mode in response to a threshold number of asynchronous ventricular pacing pulses being delivered. Responsive to the AV block detection criteria being satisfied, the control circuit switches back to operating in the atrial synchronous ventricular pacing mode.

In another example, the disclosure provides a method including setting a timer to a conduction check time interval and generating ventricular pacing pulses in an atrial synchronous ventricular pacing mode. After expiration of the conduction check time interval, the method includes switching to from the atrial synchronous ventricular pacing mode to an asynchronous ventricular pacing mode. The method further includes determining that AV block detection criteria are satisfied during the asynchronous ventricular pacing mode in response to a threshold number of ventricular pacing pulses being generated. Responsive to the AV block detection criteria being satisfied, the method includes switching back to the atrial synchronous ventricular pacing mode.

In yet another example, the disclosure provides a non-transitory, computer-readable storage medium comprising a set of instructions which, when executed by a control circuit of a pacemaker, cause the pacemaker to set a timer to a conduction check time interval and operate in an atrial synchronous ventricular pacing mode. After expiration of the conduction check time interval, the instructions cause the pacemaker to switch to an asynchronous ventricular pacing mode. The instructions may further cause the pacemaker to determine that AV block detection criteria are satisfied during the asynchronous ventricular pacing mode in response to a threshold number of ventricular pacing pulses being generated. Responsive to the AV block detection criteria being satisfied, the instructions may cause the pacemaker to switch back to operating in the atrial synchronous ventricular pacing mode.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, this disclosure describes techniques for controlling the pacing mode of an implantable cardiac pacemaker, which may be an intracardiac ventricular pacemaker, to promote AV conduction while providing atrial synchronized ventricular pacing during periods of AV block. In the illustrative examples presented herein, an intracardiac ventricular pacemaker is configured to provide single chamber ventricular pacing and, at least during an atrial synchronous ventricular pacing mode, provide dual chamber (atrial and ventricular) sensing. Atrial sensing from an intraventricular signal produced by a sensor included in the pacemaker is performed for synchronizing the ventricular pacing pulses to the sensed atrial events during periods of AV block. As described below, the atrial systolic events may be sensed from an intraventricular motion signal produced by a motion sensor included in the pacemaker. The intraventricular motion signal includes an atrial systolic event signal corresponding to atrial mechanical contraction and the active filling phase of the ventricle, sometimes referred to as the "atrial kick." In other examples, atrial event sensing may be performed using other techniques, such as sensing the far-field P-wave that is attendant to atrial depolarization, from a cardiac electrical signal sensed from within the ventricle.

The techniques disclosed herein promote AV conduction by controlling pacing mode switching in a manner that allows atrial depolarizations to conduct to the ventricles through the heart's normal conduction system when AV conduction is intact. When AV conduction block (or other conduction abnormalities) occurs, the pacemaker operates in an atrial synchronous pacing mode that relies on atrial event sensing from an intraventricular sensor signal for controlling the timing of ventricular pacing pulses, synchronized to the atrial events. As described below, the pacemaker may switch to an asynchronous ventricular pacing mode to determine if AV block is still present, based only on ventricular events without requiring atrial sensing in some examples. As used herein, an "asynchronous ventricular pacing mode" or "asynchronous pacing mode" refers to non-atrial synchronous ventricular pacing, which may be delivered in a non-atrial tracking, ventricular demand pacing mode, such as a VDI(R) or VVI(R) pacing mode. If AV block is still present, the pacemaker may switch back to the atrial synchronous ventricular pacing (with dual chamber sensing). When AV block is not detected, ventricular pacing may be controlled according to an asynchronous ventricular pacing mode with a relatively low base pacing rate so that AV conduction along the heart's intrinsic conduction system is promoted.

Figure 1:
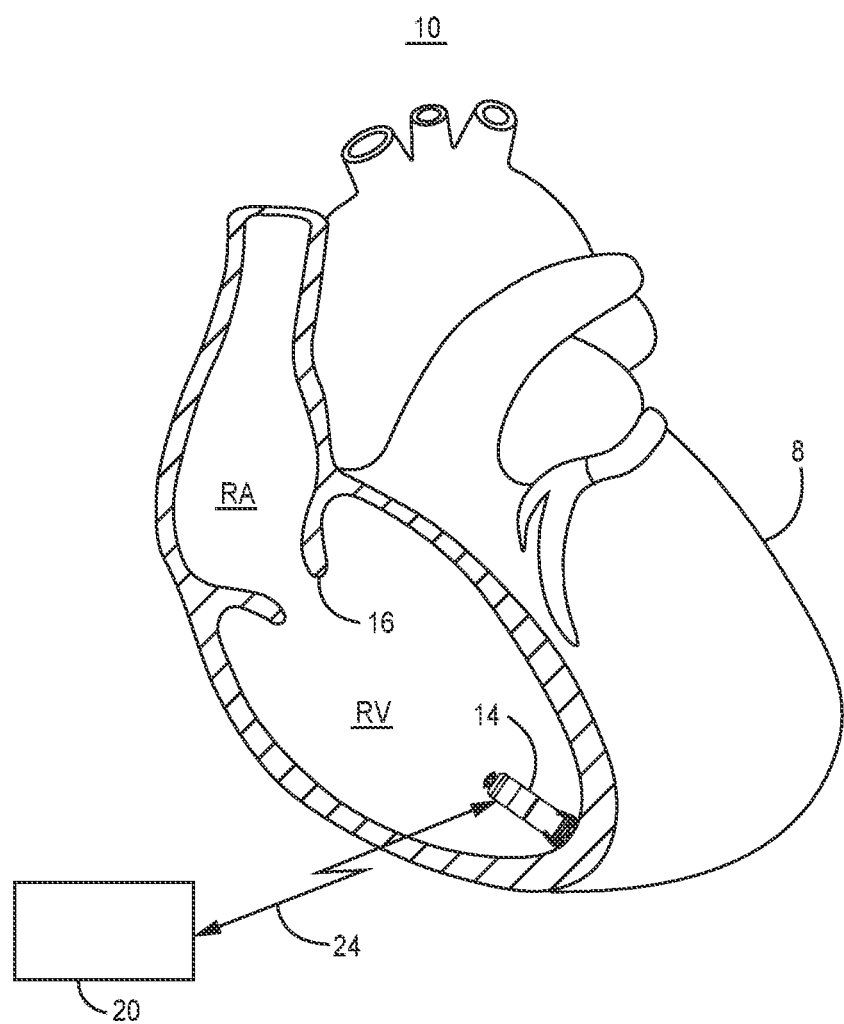
FIG. 1 is a conceptual diagram illustrating a cardiac pacing system that may be used to sense cardiac signals and provide ventricular pacing to a patient's heart in a manner that promotes AV conduction.

FIG. 1 is a conceptual diagram illustrating an implantable medical device (IMD) system 10 that may be used to sense cardiac signals and provide ventricular pacing to a patient's heart 8 in a manner that promotes AV conduction. IMD system 10 includes an intracardiac ventricular pacemaker 14. Pacemaker 14 may be a transcatheter intracardiac pacemaker which is adapted for implantation wholly within a heart chamber, e.g., wholly within the right ventricle (RV) or wholly within the left ventricle (LV) of heart 8 for sensing cardiac signals and delivering ventricular pacing pulses in a single chamber pacing mode. Pacemaker 14 may be reduced in size compared to subcutaneously implanted pacemakers and may be generally cylindrical in shape to enable transvenous implantation in a heart chamber via a delivery catheter.

In the example shown, pacemaker 14 is positioned along an endocardial wall of the RV, e.g., near the RV apex. The techniques disclosed herein are not limited to the pacemaker location shown in the example of FIG. 1 and other positions within heart 8 are possible. For example, an intracardiac ventricular pacemaker 14 may be positioned in the LV and configured to detect cardiac signals and deliver ventricular pacing to the LV using the techniques disclosed herein. Pacemaker 14 may be positioned within the right ventricle or left ventricle to provide respective right ventricular or left ventricular pacing and for sensing atrial signals from within the ventricular chamber for facilitating atrial synchronous ventricular pacing.

Pacemaker 14 is capable of producing electrical stimulation pulses, e.g., pacing pulses, delivered to heart 8 via one or more electrodes on the outer housing of the pacemaker. Pacemaker 14 is configured to generate and deliver ventricular pacing pulses and sense a cardiac electrical signal using housing based electrodes for producing a ventricular electrogram (EGM) signal. The cardiac electrical signals may be sensed using the housing based electrodes that are also used to deliver pacing pulses to the heart 8.

Pacemaker 14 is configured to control the delivery of ventricular pacing pulses to the ventricle in a manner that promotes synchrony between atrial systole and ventricular systole, e.g., by maintaining a target atrioventricular (AV) interval between a sensed atrial systolic event and ventricular pacing pulses while operating in an atrial synchronous ventricular pacing mode. Pacemaker 14 senses atrial events from an intraventricular signal produced by a sensor included in or on the pacemaker and controls ventricular pacing pulse delivery to maintain a desired AV interval between atrial systolic events and ventricular pacing pulses delivered to cause ventricular depolarization and ventricular systole. The atrial synchronous ventricular pacing mode may be referred to as a "VDD" pacing mode since single chamber ventricular pacing is being delivered with dual chamber sensing and a dual response is provided to sensed events, either a pacing pulse is triggered in response to an atrial sensed event or inhibited in response to a ventricular sensed event, e.g., and R-wave.

The atrial synchronous ventricular pacing mode is provided to promote a more normal heart rhythm during periods of AV block. In patients that may have intermittent AV block (or other conduction abnormalities), pacemaker 14 operates to promote AV conduction along the normal conduction pathways of the heart by periodically switching to an asynchronous ventricular pacing mode, e.g., VVI or VDI pacing mode. If AV conduction is determined to be present, the pacemaker remains in the asynchronous pacing mode with a relatively low base pacing rate to promote conduction of atrial depolarizations to the ventricles via the heart's natural conduction system. If AV block is determined to be present, the pacemaker switches back to the atrial synchronous pacing mode, e.g., VDD pacing mode.

In some examples, pacemaker 14 includes a motion sensor, such as an accelerometer, that produces an intraventricular motion signal including atrial systolic event signals corresponding to the active filling phase of ventricular diastole. The motion signal produced by an accelerometer implanted within the RV, for example, includes motion signals caused by ventricular and atrial events. For instance, acceleration of blood flowing into the RV through the tricuspid valve 16 between the right atrium (RA) and RV caused by atrial systole may be detected by pacemaker 14 from the signal produced by an accelerometer included in pacemaker 14. Other motion signals detected by pacemaker 14, such as motion caused by ventricular contraction, motion caused by ventricular relaxation, and motion caused by passive filling of the ventricle are described below in conjunction with FIG. 4. Pacemaker 14 may perform atrial event sensing to enable atrial synchronous ventricular pacing by sensing atrial events from an intraventricular motion signal.

In other examples, pacemaker 14 may sense atrial systolic events by sensing atrial P-waves that are attendant to atrial depolarizations. P-waves are relatively low amplitude signals in the near-field RV electrical signal received by pacemaker 14 (e.g., compared to the near-field R-waves) and therefore can be difficult to consistently detect from the cardiac electrical signal acquired by pacemaker 14 when implanted in a ventricular chamber. Atrial synchronous ventricular pacing by pacemaker 14 may not be reliable when based solely on a cardiac electrical signal received by pacemaker 14. According to the techniques disclosed herein, the pacemaker 14 may therefore include a motion sensor, such as an accelerometer, and be configured to detect an atrial event corresponding to atrial mechanical activation or atrial mechanical systole using a signal from the motion sensor.

A target AV interval may be a programmed value selected by a clinician and is the time interval from the detection of the atrial event until delivery of the ventricular pacing pulse. The target AV interval may be identified as being hemodynamically optimal for a given patient based on clinical testing or assessments of the patient or based on clinical data from a population of patients. The target AV interval may be determined to be optimal based on relative timing of electrical and mechanical events as identified from the cardiac electrical signal received by pacemaker 14 and the motion sensor signal received by pacemaker 14. The AV interval may be set to 10 to 50 ms, in some examples, to control pacemaker 14 to deliver a ventricular pacing pulse synchronized to the atrial event sensed from the motion signal.

Pacemaker 14 may be capable of bidirectional wireless communication with an external device 20 for programming the AV pacing interval and other pacing control parameters as well as both electrical and mechanical event sensing parameters utilized for detecting ventricular events (e.g., R-waves) from the cardiac electrical signal and atrial systolic events from the intraventricular motion sensor signal. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemaker 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemaker 14 using external device 20.

External device 20 is configured for bidirectional communication with implantable telemetry circuitry included in pacemaker 14. External device 20 establishes a wireless communication link 24 with pacemaker 14. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate pacemaker 14 to establish and maintain a communication link 24, and in other examples external device 20 and pacemaker 14 may be configured to communicate using a distance telemetry algorithm and circuitry that does not require the use of a programming head and does not require user intervention to maintain a wireless communication link. An example RF telemetry communication system that may be implemented in system 10 is generally disclosed in U.S. Pat. No. 5,683,432 (Goedeke, et al.), hereby incorporated herein by reference in its entirety. External device 20 may display data and information relating to pacemaker functions to a user for reviewing pacemaker operation and programmed parameters as well as EGM signals transmitted from pacemaker 14, motion sensor signals produced by pacemaker 14, or other physiological data that is produced by and retrieved from pacemaker 14 during an interrogation session.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a remote patient database may be configured to utilize the presently disclosed techniques to enable a clinician to review EGM, motion sensor, and marker channel data and authorize programming of sensing and therapy control parameters in pacemaker 14, e.g., after viewing a visual representation of EGM, motion sensor signal and marker channel data (as show in FIG. 7 as an example).

Figure 2:
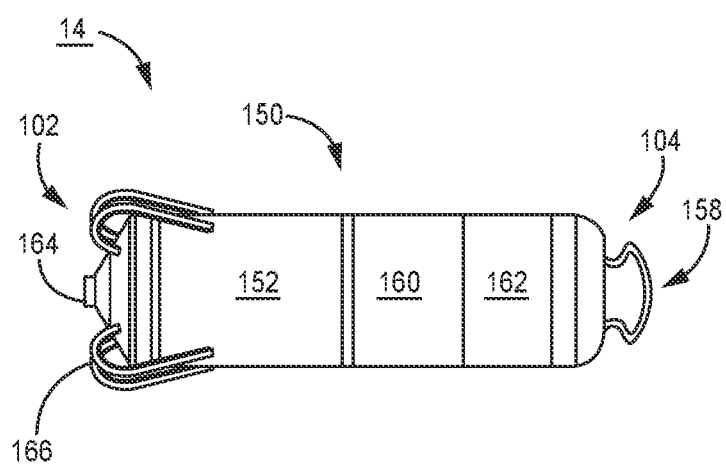
FIG. 2 is a conceptual diagram of the pacemaker shown in FIG. 1.

FIG. 2 is a conceptual diagram of the intracardiac pacemaker 14 shown in FIG. 1. Pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 defining a ring electrode that is electrically isolated from the other portions of the housing 150 as generally shown in FIG. 2. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 14 as described below in conjunction with FIG. 3. A motion sensor may be implemented as an accelerometer included in control electronics subassembly 152 and enclosed within housing 150 in some examples. The accelerometer provides a signal to a processor included in control electronics subassembly 152 for signal processing and analysis for sensing atrial systolic events for timing ventricular pacing pulses during atrial synchronous ventricular pacing as described below.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned U.S. Pat. No. 9,775,982 (Grubac, et al.), hereby incorporated herein by reference in its entirety.

Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a ventricular heart chamber.

Figure 3:
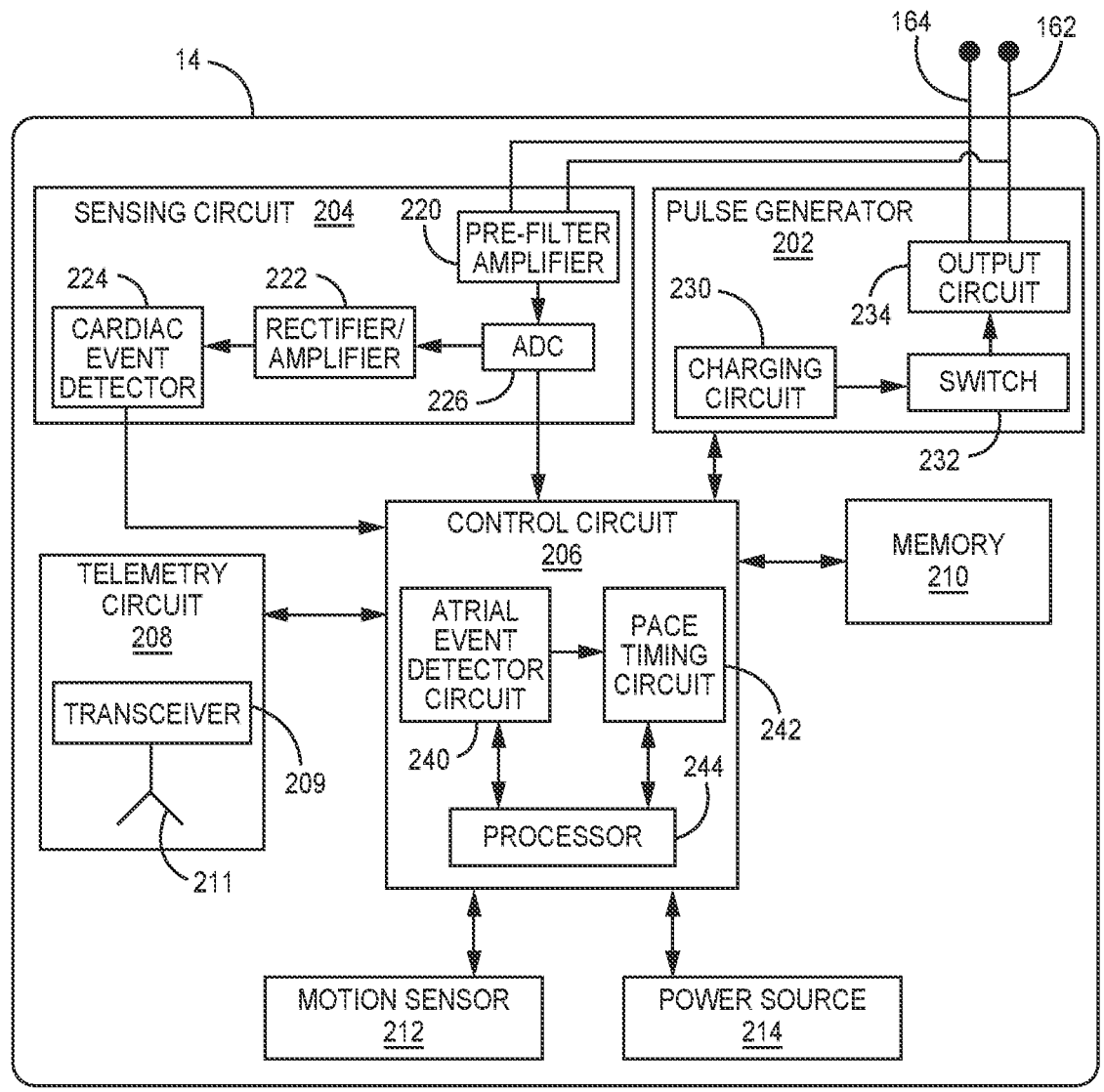
FIG. 3 is a schematic diagram of an example configuration of the pacemaker shown in FIG. 1.

FIG. 3 is a schematic diagram of an example configuration of pacemaker 14 shown in FIG. 1. Pacemaker 14 includes a pulse generator 202, a cardiac electrical signal sensing circuit 204 (also referred to herein as "sensing circuit 204") a control circuit 206, memory 210, telemetry circuit 208, motion sensor 212 and a power source 214. The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Motion sensor 212 is implemented as an accelerometer in the examples described herein and may also be referred to herein as "accelerometer 212." Motion sensor 212 is not limited to being an accelerometer, however, and other motion sensors may be utilized successfully in pacemaker 14 for detecting cardiac motion signals according to the techniques described herein. Examples of motion sensors that may be implemented in motion sensor 212 include piezoelectric sensors and MEMS devices.

Motion sensor 212 may be a single axis, one-dimensional sensor or a multi-axis sensor, e.g., a two-dimensional or three-dimensional sensor, with each axis providing a signal that may be analyzed individually or in combination for detecting cardiac mechanical events. Motion sensor 212 produces an electrical signal correlated to motion or vibration of sensor 212 (and pacemaker 14), e.g., when subjected to flowing blood, cardiac motion and patient body motion due to physical activity such as exercise and activities of daily living or other motion imparted on the patient such as riding in a car. The motion sensor 212 may include filters, amplifiers, rectifiers, an analog-to-digital converter (ADC) and/or other components for producing a motion signal passed to control circuit 206. For example, each vector signal corresponding to each individual axis of a multi-axis accelerometer may be filtered by a high pass filter, e.g., a 10 Hz high pass filter, and rectified for use by atrial event detector circuit 240 for sensing atrial systolic events. The high pass filter may be lowered (e.g., to 5 Hz) if needed to detect atrial event signals that have lower frequency content. In some examples, high pass filtering is performed with no low pass filtering. In other examples, each accelerometer axis signal is filtered by a low pass filter, e.g., a 30 Hz low pass filter, with or without high pass filtering. The motion sensor may include separate filtering of the accelerometer signal for passing a motion signal to control circuit 206 for use in detecting patient physical activity level to enable rate responsive ventricular pacing to meet the patient's metabolic demand.

One example of an accelerometer for use in implantable medical devices is generally disclosed in U.S. Pat. No.

5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 14 due to ventricular and atrial events and patient physical activity.

Sensing circuit 204 is a cardiac electrical signal sensing circuit configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to ADC 226. ADC 226 may pass a multi-bit, digital electrogram (EGM) signal to control circuit 206 for use by atrial event detector circuit 240 in identifying ventricular electrical events (e.g., R-waves or T-waves) and/or atrial electrical events, e.g., P-waves. Identification of cardiac electrical events may be used for detecting atrial systolic events from the motion sensor signal, e.g., by setting atrial blanking and sensing windows relative to sensed R-waves. The digital signal from ADC 226 may be passed to rectifier and amplifier circuit 222, which may include a rectifier, bandpass filter, and amplifier for passing the filtered and rectified cardiac electrical signal to cardiac event detector 224.

Cardiac event detector 224 may include a sense amplifier or other detection circuitry that compares the incoming rectified, cardiac electrical signal to an R-wave detection threshold, which may be an auto-adjusting threshold. When the incoming signal crosses the R-wave detection threshold, the cardiac event detector 224 produces an R-wave sensed event signal that is passed to control circuit 206. In other examples, cardiac event detector 224 may receive the digital output of ADC 226 for detecting R-waves by a comparator, morphological signal analysis of the digital EGM signal or other R-wave detection techniques. R-wave sensed event signals passed from cardiac event detector 224 to control circuit 206 may be used for scheduling ventricular pacing pulses by pace timing circuit 242 during asynchronous ventricular pacing, determining ventricular rate intervals or RR intervals, and for use in identifying the timing of ventricular electrical events by atrial event detector circuit 240 for facilitating detection of atrial systolic events from a signal received from motion sensor 212.

In some examples, cardiac event detector 224 is configured to sense P-waves from the cardiac electrical signal received by electrodes 162 and 164 (and/or electrodes carried by a sensing extension extending away from housing 150). Cardiac event detector 224 may compare the incoming signal to a P-wave sensing threshold and produce a P-wave sensed event signal passed to control circuit 206 in response to a threshold crossing. When pacemaker 14 is configured to sense R-waves and P-waves, sensing circuit 204 may include two different sensing channels, each including a pre-filter/amplifier, ADC, rectifier/amplifier and cardiac event detector configured to amplify and filter cardiac electrical signals received via one or two different sensing electrode pairs for separately sensing R-waves and P-waves from the cardiac electrical signals. P-wave sensing may be used for verifying atrial events sensed from a motion sensor signal or vice versa. In some examples, P-wave sensed event signals are used by control circuit 206 for starting an AV interval for controlling atrial synchronous ventricular pacing pulses delivered by pulse generator 202.

Control circuit 206 includes an atrial event detector circuit 240, pace timing circuit 242, and processor 244. Atrial event detector circuit 240 is configured to detect atrial mechanical events from a signal received from motion sensor 212. In some examples, one or more ventricular mechanical events may be detected from the motion sensor signal in a given cardiac cycle to facilitate positive detection of the atrial systolic event from the motion sensor signal during the ventricular cycle.

Control circuit 206 may receive R-wave sensed event signals, P-wave sensed event signals, and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses during atrial synchronous ventricular pacing or scheduling ventricular pacing pulses when pacemaker 14 is operating in a non-atrial tracking (asynchronous) ventricular pacing mode. As described below, R-wave sensed event signals may be used by control circuit 206 for determining if AV conduction is intact during an asynchronous ventricular pacing mode.

R-wave sensed event signals may be passed to atrial event detector circuit 240 for use in setting atrial blanking periods and/or time windows used by control circuit 206 in sensing atrial systolic events from the motion sensor signal. Atrial event detector circuit 240 receives a motion signal from motion sensor 212 and may start an atrial blanking period in response to a ventricular electrical event, e.g., an R-wave sensed event signal from sensing circuit 204 or delivery of a pacing pulse by pulse generator 202. The blanking period may correspond to a time period after the ventricular electrical event during which ventricular mechanical events, e.g., corresponding to ventricular contraction and isovolumic relaxation are expected to occur. Motion signal peaks that occur during the atrial blanking period are not sensed as atrial events to avoid falsely sensing a ventricular motion signal event as the atrial systolic event.

Atrial event detector circuit 240 determines if the motion sensor signal satisfies atrial mechanical event detection criteria outside of the atrial blanking period. The motion sensor signal during the atrial blanking period may be monitored by atrial event detector circuit 240 and/or processor 244 for the purposes of detecting ventricular mechanical events, which may be used for confirming or validating atrial systolic event detection or detecting ventricular event intervals in some examples. As such, ventricular mechanical event detection windows may be set during the atrial blanking period and may be set according to predetermined time intervals following identification of a ventricular electrical event.

Atrial event detector circuit 240 may set time windows corresponding to the passive ventricular filling phase and the active ventricular filling phase based on the timing of a preceding ventricular electrical event, either an R-wave sensed event signal or a ventricular pacing pulse. A motion sensor signal crossing of an atrial event sensing threshold during either of these windows may be detected as the atrial systolic event. As described below, two different atrial event sensing threshold values may be established for applying during the passive filling phase window and after the passive filling phase window (during an active filling phase window).

Atrial event detector circuit 240 passes an atrial event detection signal to processor 244 and/or pace timing circuit 242 in response to detecting an atrial event. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242. Other examples of atrial event sensing or detection for use in controlling atrial synchronized ventricular pacing by an intracardiac ventricular pacemaker are generally disclosed in commonly assigned U.S. Pat. No. 9,399,140 (Cho, et al.), U.S. Pat. No. 10,328,270 (Demmer, et al) and U.S. Pat. No. 10,350,317 (Cao, et al.), all of which are incorporated herein by reference in their entirety.

Pace timing circuit 242 (or processor 244) may additionally receive R-wave sensed event signals from cardiac event detector 224 for use in controlling the timing of pacing pulses delivered by pulse generator 202. Pace timing circuit 242 may include a lower pacing rate interval timer for controlling a lower ventricular pacing rate. For example, if an atrial systolic event is not detected from the motion sensor signal triggering a ventricular pacing pulse at the programmed AV pacing interval, a ventricular pacing pulse may be delivered by pulse generator 202 upon expiration of the lower pacing rate interval to prevent ventricular asystole and maintain a minimum ventricular rate. In order to avoid abrupt changes in ventricular rate, control circuit 206 may be configured to set the lower ventricular pacing rate interval to a rate smoothing interval during the atrial synchronous ventricular pacing mode and/or upon switching to the atrial synchronous ventricular pacing mode from an asynchronous ventricular pacing mode. The rate smoothing interval may be determined based on one or more preceding ventricular event intervals. For example, a ventricular pacing pulse delivered in the absence of a sensed atrial event during VDD pacing may be delivered at an interval that is within a predetermined interval of preceding Vpace-to-Vpace intervals or a median RR interval, e.g., within 150 ms or within 100 ms of the actual preceding ventricular rate interval(s).

At times, control circuit 206 may control pulse generator 202 in an asynchronous ventricular pacing mode, e.g., for checking for AV conduction and as long as AV block is not detected. During the asynchronous ventricular pacing mode, pace timing circuit 242 may set a VV pacing interval to a base pacing rate interval corresponding to a programmed minimum base rate, which may be 60 pulses per minute or less, e.g., 40 pulses per minute. As further described below, control circuit 206 may remain in the asynchronous pacing mode as long as AV block detection criteria remain unsatisfied. If AV block is detected, however, control circuit 206 may switch back to the atrial synchronous ventricular pacing mode to promote AV synchrony. At times, pacemaker 14 may adjust the VV pacing interval during asynchronous ventricular pacing to a temporary pacing interval set based on a patient physical activity metric to provide rate responsive ventricular pacing that supports the metabolic demand of the patient.

Control circuit 206 may determine the patient activity metric from the motion signal received from motion sensor 212 at a desired frequency for use in determining a sensor-indicated pacing rate (SIR). The SIR may vary between the programmed minimum base rate during periods of rest (minimal activity metric) and a maximum upper pacing rate during periods of maximum exertion. The SIR may be controlled according to a SIR transfer function as described below, which may include different rates of change of the SIR over different ranges of the activity metric.

In some examples, the activity metric is determined as an activity count. In these instances, control circuit 206 includes a counter to track the activity count as the number of times the signal from motion sensor 212 crosses a threshold during an activity count interval, for example a 2-second interval. The count at the end of each activity count interval is correlated to patient body motion during the activity count interval and is therefore correlated to patient metabolic demand. The threshold applied to the motion sensor signal, which when crossed by the motion sensor signal causes the activity count to be increased, may be a default or programmable threshold or may be an automatically adjusted threshold. Example methods for obtaining an activity count over an n-second interval and for adjusting the motions sensor signal threshold used for obtaining the activity count are generally disclosed in U.S. Pat. No. 5,720,769 (van Oort), incorporated herein by reference in its entirety.

In other examples, an activity metric may be obtained from the motion sensor signal by integrating or summing motion signal sample points over an activity count interval, e.g., a two-second interval though longer or shorter intervals of time may be used for determining an activity metric. The activity metric may be converted to a target heart rate to meet the patient's metabolic demand. The target heart rate may be converted to a SIR based on a SIR transfer function that includes a base pacing rate set point and an activities of daily living (ADL) range. As long as the activity metric is at or below the base pacing rate set point, the SIR remains at the base pacing rate.

As the activity count increases above the base pacing rate set point, the SIR may be determined according to the SIR transfer function slope or profile up to the ADL range. As long as the patient activity metric (and resulting target heart rate) remains between a lower and upper boundary of the ADL range, the SIR is set to an ADL rate, which is greater than the base pacing rate and is expected to provide adequate pacing support to the patient during normal daily activities, such as moving about the home, driving a car, light tasks, etc.

If the activity metric and resultant target heart rate rises to be greater than the ADL range, the SIR is increased according to a slope or profile of the SIR transfer function over the range from the upper boundary of the ADL range to reach the target heart rate, up to the maximum upper rate set point. The SIR is set to the maximum upper pacing rate for all activity metrics greater than the maximum upper rate set point. Each of the base pacing rate set point, the ADL range and the maximum upper rate set point may be tailored to a patient's particular needs based on activity metric history. In order to avoid abrupt changes in pacing rate, the target heart rate may be determined from the patient activity metric, and the SIR may be determined from the target rate according to the transfer function that controls how quickly the SIR accelerates or decelerates up to or down to the target rate as patient activity increases or decreases, respectively. Examples of methods for establishing a SIR transfer function applied to patient activity metrics determined from an intraventricular motion signal are generally disclosed in U.S. Pat. No. 9,724,518 (Sheldon, et al.), incorporated herein by reference in its entirety.

Other types of sensors that may produce a signal correlated to patient activity include sensors of respiratory activity, such as minute ventilation, blood or tissue oxygen saturation, as examples. Other types of patient physical activity sensors may be used for providing control circuit 206 with a signal correlated to metabolic demand for use in determining a SIR and enabling rate responsive pacing. Various examples of other types of implantable sensors that may be implemented with a rate responsive pacemaker for controlling pacing rate based on metabolic demand are generally described in U.S. Pat. No. 5,755,740 (Nappholz), U.S. Pat. No. 5,507,785 (Deno), and U.S. Pat. No. 5,312,454 (Roline). The techniques disclosed herein for controlling a rate responsive asynchronous ventricular pacing mode may be used in combination with any type of patient physical activity sensor that produces a signal that indicates patient activity level correlated to metabolic demand.

Processor 244 may retrieve programmable pacing control parameters, such as pacing pulse amplitude and pacing pulse width, which are passed to pulse generator 202 for controlling pacing pulse delivery from memory 210. In addition to providing control signals to pace timing circuit 242 and pulse generator 202 for controlling pacing pulse delivery, processor 244 may provide sensing control signals to sensing circuit 204 (e.g., R-wave sensing threshold, P-wave sensing threshold, sensitivity, and/or various blanking and refractory intervals applied to the cardiac electrical signal) and to atrial event detector circuit 240 for sensing atrial events from the motion sensor signal as described below.

Pulse generator 202 generates electrical pacing pulses that are delivered to the RV of the patient's heart via cathode electrode 164 and return anode electrode 162. Pulse generator 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of a pacing interval, e.g., an AV pacing interval, a VV rate smoothing interval, a SIR interval, or VV base pacing rate interval, and kept closed for a programmed pacing pulse width to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 for generating and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media. Memory 210 may store timing intervals and other data used by control circuit 206 to control the delivery of pacing pulses by pulse generator 202 according to the techniques disclosed herein.

Power source 214 may correspond to battery subassembly 160 shown in FIG. 2 and provides power to each of the other circuits and components of pacemaker 14 as required. Power source 214 may include one or more energy storage devices, such as one or more rechargeable or non-rechargeable batteries. The connections between power source 214 and other pacemaker circuits and components are not shown in FIG. 3 for the sake of clarity but are to be understood from the general block diagram of FIG. 3. For example power source 214 may provide power to charging circuit 230 for charging a holding capacitor to a pacing voltage amplitude, current to switch 232 and other circuitry included in pulse generator 202 as needed to generate and deliver pacing pulses. Power source 214 also provides power to telemetry circuit 208, motion sensor 212, and sensing circuit 204 as needed as well as memory 210.

Telemetry circuit 208 includes a transceiver 209 and antenna 211 for transferring and receiving data, e.g., via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and programming commands for performing atrial event detection and ventricular pacing control according to the techniques disclosed herein may be received by telemetry circuit 208 and stored in memory 210 for access by control circuit 206.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal and ventricular pacing control operations performed by pacemaker 14 may be implemented in control circuit 206 executing instructions stored in memory 210 and relying on input from sensing circuit 204 and motion sensor 212.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modern pacemaker, given the disclosure herein, is within the abilities of one of skill in the art.

Figure 4:
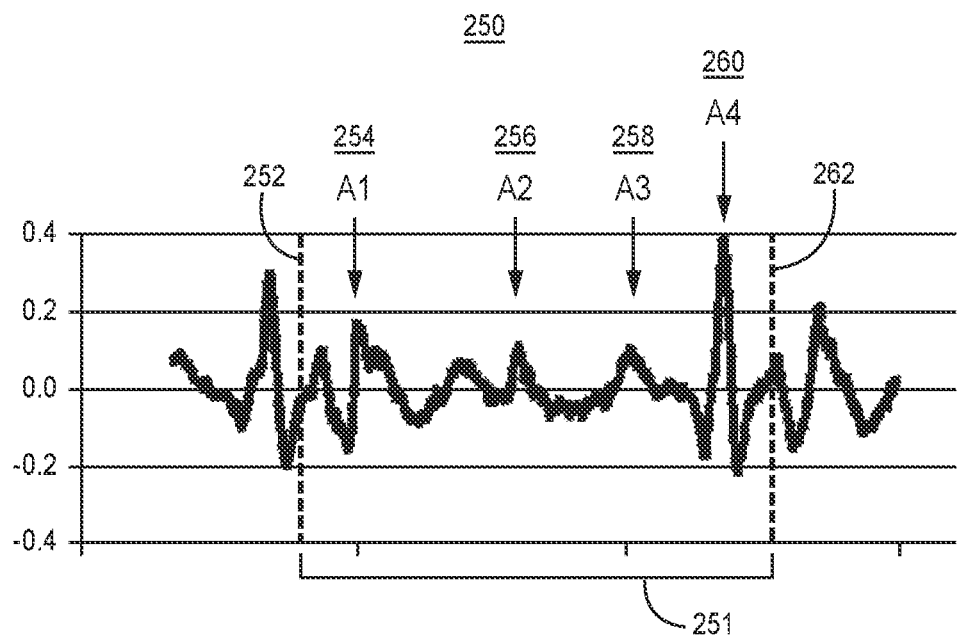
FIG. 4 is an example of a motion sensor signal that may be acquired by a motion sensor included in the pacemaker of FIG. 1.

FIG. 4 is an example of a motion sensor signal 250 that may be produced by motion sensor 212 over a cardiac cycle. Vertical dashed lines 252 and 262 denote the timing of two consecutive ventricular events (an intrinsic ventricular depolarization or a ventricular pace), marking the respective beginning and end of the ventricular cycle 251. The motion signal includes an A1 event 254, an A2 event 256, an A3 event 258 and an A4 event 260. The A1 event 254 is an acceleration signal (in this example when motion sensor 212 is implemented as an accelerometer) that occurs during ventricular contraction and marks the approximate onset of ventricular mechanical systole. The A1 event is also referred to herein as a "ventricular contraction event." The A2 event 256 is an acceleration signal that may occur during closure of the aortic and pulmonic valves and marks the approximate offset or end of ventricular mechanical systole. The A2 event may also mark the beginning of ventricular diastole and is generally an indication of the isovolumic relaxation phase of the ventricles that occurs with aortic and pulmonic valve closure. The A3 event 258 is an acceleration signal that occurs during passive ventricular filling and marks ventricular mechanical diastole. The A3 event is also referred to herein as the "ventricular passive filling event."

The A4 event 260 is an acceleration signal that occurs during atrial contraction and active ventricular filling and marks atrial mechanical systole. The A4 event 260 may also referred to herein as the "atrial systolic event" or merely the "atrial event," and is the atrial systolic event that is detected from motion sensor signal 250 by atrial event detector circuit 240 for controlling pace timing circuit 242 to trigger ventricular pacing pulse delivery by starting an AV pacing interval in response to detecting the A4 event 260. In some examples, control circuit 206 may be configured to detect one or more of the A1, A2, and A3 events from motion sensor signal 250, for at least some ventricular cardiac cycles, for use in positively detecting the A4 event 260 and setting atrial event detection control parameters. The A1, A2 and/or A3 events may be detected and characterized to avoid false detection of A4 events and promote reliable A4 event detection for proper timing of atrial-synchronized ventricular pacing pulses.

Figure 5:
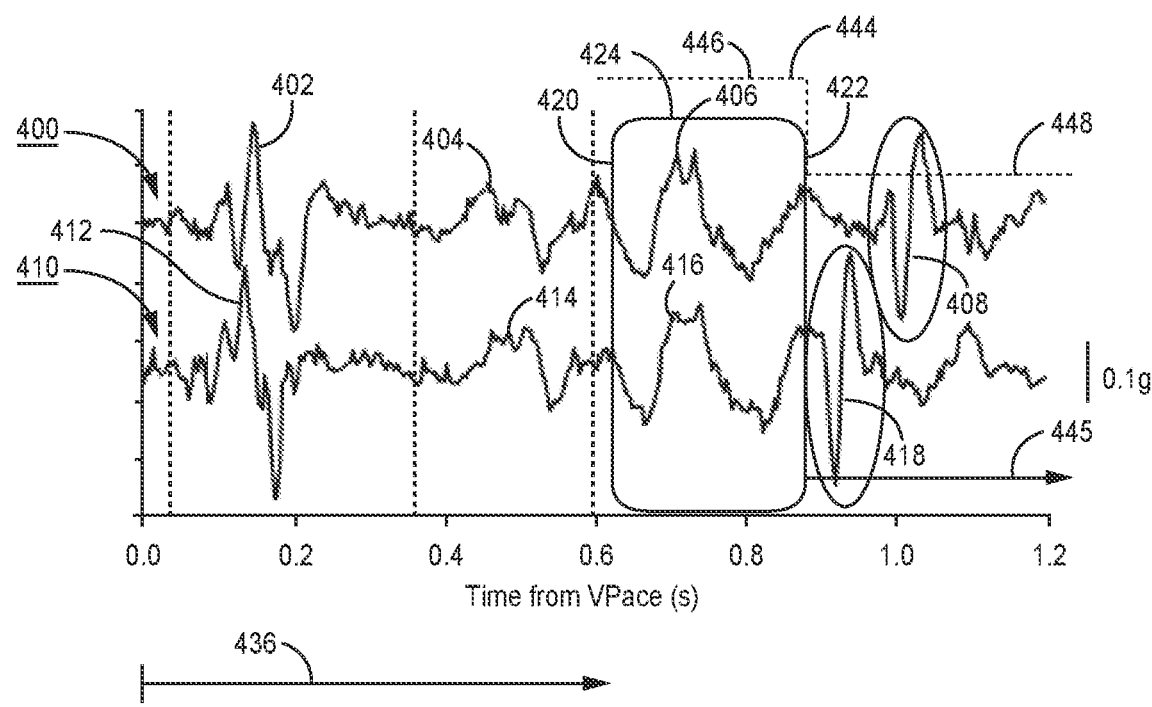
FIG. 5 is an example of motion sensor signals acquired over two different cardiac cycles.

FIG. 5 depicts example motion sensor signals 400 and 410 acquired over two different cardiac cycles. A ventricular pacing pulse is delivered at time 0.0 seconds for both cardiac cycles. The top sensor signal 400 is received over one cardiac cycle and the bottom sensor signal 401 is received over a different cardiac cycle. The two signals 400 and 410 are aligned in time at 0.0 seconds, the time of the ventricular pacing pulse delivery. While motion signals 400 and 410 and motion signal 250 of FIG. 4 are shown as raw accelerometer signals, it is recognized that control circuit 80 may receive a filtered, amplified and rectified signal from motion sensor 212 for detecting atrial events by atrial event detector circuit 240.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 and the A3 events 406 and 416 (occurring during passive ventricular filling) are well-aligned in time. Since the A1, A2 and A3 events are ventricular events, occurring during ventricular contraction, ventricular isovolumic relaxation, and passive ventricular filling, respectively, these events are expected to occur at relatively consistent intervals following a ventricular electrical event, the ventricular pacing pulse in this example, and relative to each other. The time relationship of the A1, A2 and A3 events may be different following a ventricular pacing pulse compared to following a sensed intrinsic R-wave; however, during a stable paced or intrinsic ventricular rhythm, the relative timing of A1, A2 and A3 events to each other and the immediately preceding ventricular electrical event is expected to be consistent.

The A4 events 408 and 418 of the first and second motion sensor signals 400 and 410 respectively are not aligned in time. The A4 event occurs due to atrial systole and as such the time interval to the A4 event following the immediately preceding ventricular electrical event (sensed R-wave or ventricular pacing pulse) and the preceding A1 through A3 events may vary between cardiac cycles.

The consistency of the timing of the A1 through A3 events relative to each other and the immediately preceding ventricular electrical event may be used for determining an atrial blanking period 436 and increasing confidence in reliably detecting A4 events 408 and 418. The atrial systolic event is not detected during the atrial blanking period 436 which extends from the ventricular electrical event (at time 0.0) to an estimated onset of ventricular diastole, for example. An A3 sensing window 424 may be set having a starting time 420 corresponding to the end of the atrial blanking period 436 and an ending time 422. The atrial blanking interval 436 may be 600 ms, as one example with no limitation intended, and the A3 window 424 may extend 200 ms or other selected time interval after the atrial blanking interval 436.

A4 events 408 and 418 may be detected based on a multi-level A4 detection threshold 444. As seen by the lower motion sensor signal 410, the A4 event 418 may occur earlier after the A3 window 424 due to changes in atrial rate. In some instances, as the atrial rate increases, the A4 event 418 may occur within the A3 window 424. When this occurs, the A3 event 416 and the A4 event 418 may fuse as passive and active ventricular filling occur together. The fused A3/A4 event may have a high amplitude, even greater than the amplitude of either the A3 event 416 or the A4 event 418 when they occur separately. As such, in some examples the A4 detection threshold 444 includes a first, higher A4 threshold amplitude 446 established for detecting an early A4 event that is fused with the A3 event during the A3 window 424. A second, lower A4 threshold amplitude 448 may be established for detecting relatively later A4 events, after the ending time 422 of the A3 window 424. An A4 window 445 may extend from the end of the A3 window 424 until an atrial event is sensed or a ventricular event occurs, whichever occurs first. The earliest crossing of the A4 detection threshold 444 by the motion sensor signal after the starting time 420 of the A3 window (or after the expiration of the atrial blanking period 436) may be sensed as the atrial systolic event. Various examples of an intracardiac pacemaker configured to detect atrial systolic events from a motion sensor signal for delivering atrial synchronous ventricular pacing are disclosed in commonly-assigned U.S. Publication No. 2018/0085589 (Splett et al.), U.S. Pat. No. 10,449,366 (Splett, et al.), U.S. Pat. No. 10,286,214 (Demmer, et al.), U.S. Pat. No. 10,207,116 (Sheldon, et al.), and U.S. Pat. No. 10,328,270 (Demmer, et al.), all of which are incorporated herein by reference in their entirety. The techniques disclosed herein for controlling the pacing mode for promoting AV conduction and minimize ventricular pacing may be implemented in any of the examples presented in the foregoing incorporated references.

Figure 6:
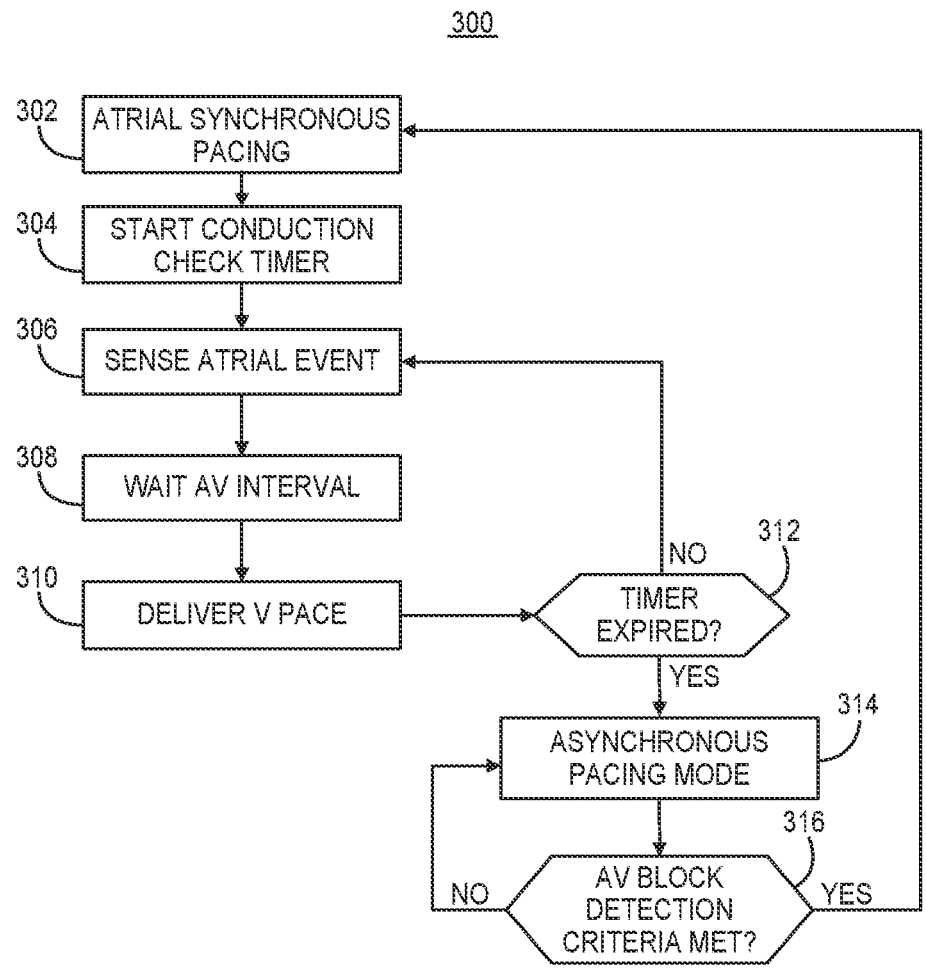
FIG. 6 is a flow chart of a method performed by the pacemaker of FIG. 1 for controlling ventricular pacing to promote AV conduction during periods of intact AV conduction and provide atrial synchronous ventricular pacing when AV conduction is blocked according to one example.

FIG. 6 is a flow chart 300 of a method performed by pacemaker 14 for controlling pacing mode to promote AV conduction during periods of intact AV conduction and provide atrial synchronous ventricular pacing when AV conduction is blocked. At block 302, control circuit 206 starts operation in an atrial synchronous ventricular pacing mode, e.g., a VDD pacing mode. The VDD pacing mode may be the programmed pacing mode of pacemaker 14. During VDD pacing, ventricular pacing is synchronized to sensed atrial events promoting AV synchrony even in the presence of AV conduction block. Minimum ventricular pacing may be enabled in the VDD pacing mode to allow mode switching to an asynchronous ventricular pacing mode including a very low base ventricular pacing rate, e.g., 60 pulses per minute or less, 50 pulses per minute or less, 40 pulses per minute or less or even 30 pulses per minute, to allow AV conduction to occur along natural conduction pathways when the atrial rate is greater than the base ventricular pacing rate and AV conduction is intact, thereby inhibiting ventricular pacing.

In order to control when switching to the asynchronous ventricular pacing mode occurs, control circuit 206 starts a conduction check timer at block 304. The conduction check timer may be set to a starting time period, e.g., one minute, five minutes or other selected starting time period, that is relatively short so that a conduction check is initially performed after a relatively short time period, e.g., 10 minutes or less, of atrial synchronous ventricular pacing. In other examples, the conduction check timer may be set to relatively longer starting time period, e.g., 15 minutes, 30 minutes, one hour, several hours, one day, or other selected time period.

While the conduction check time period is running, pacemaker 14 operates in the atrial synchronous pacing mode by sensing an atrial event at block 306, setting an AV pacing interval at block 308, and delivering a ventricular pacing pulse at block 310 upon the expiration of the AV interval at block 310. As described above in conjunction with FIG. 5, the atrial event may be sensed by control circuit 206 from the motion signal received from motion sensor 212. Atrial synchronous ventricular pacing may continue in this manner until the conduction check timer expires at block 312.

In response to the timer expiring at block 312, control circuit 206 switches the pacing mode from the atrial synchronous pacing mode to an asynchronous pacing mode, e.g., VVI or VDI pacing mode, at block 314. During the asynchronous pacing mode, the base ventricular pacing rate may be set to a relatively low rate, e.g., 40 pulses per minute, in order to promote conduction of atrial depolarizations to the ventricles before a ventricular pacing pulse is scheduled to be delivered at the base pacing rate interval (VV pacing interval). The base ventricular pacing rate may be a fixed value or a user-programmable value. If a ventricular event is not sensed, e.g., if control circuit 206 does not receive an R-wave sensed event signal from sensing circuit 204 before the VV pacing interval corresponding to the base pacing rate expires, control circuit 206 controls pulse generator 202 to deliver a ventricular pacing pulse. Ventricular pacing is delivered at the base rate in the absence of an R-wave sensed event signal to avoid asystole and provide ventricular pacing support at the base pacing rate if the patient is experiencing AV block.

At block 316, control circuit 206 determines if AV block detection criteria are met based on ventricular events. AV block may be detected based on the frequency of ventricular pacing delivered after switching to the asynchronous pacing mode. During the asynchronous pacing mode, atrial event sensing may be disabled or ignored in some examples. Disabling atrial event sensing from the motion signal during the asynchronous pacing mode may extend the useful life of pacemaker 14 compared to the pacemaker longevity when atrial event sensing continues to be enabled during the asynchronous pacing mode. Pacemaker longevity may be extended by disabling atrial event sensing during the asynchronous pacing mode to conserve the power that would normally be required by motion sensor 212 for producing the motion signal for atrial event sensing. As such, the decision at block 316 as to whether AV block is being detected may be based solely on ventricular events, paced or sensed, without requiring atrial event sensing. Control circuit 206 may identify ventricular events, paced and/or sensed, and compare the number of paced and sensed ventricular events to AV block criteria without sensing or identifying atrial events. If ventricular pacing occurs at the base pacing rate, a conducted depolarization has not occurred so that the ventricular pacing pulse delivery is evidence of AV block. In one example, if at least X pacing pulses are delivered out of Y consecutive ventricular events, AV block detection criteria are met at block 316. For instance, if two pacing pulses are delivered during four consecutive ventricular events, AV block is detected at block 316. In other examples, if four paced events out of eight consecutive ventricular events, two out of two, or other X of Y (where X is less than or equal to Y) criteria are reached, AV block is detected at block 316. The AV block detection criteria may require as few as one ventricular pacing pulse delivery at the base rate for detecting AV block and may require two or more ventricular pacing pulses in other examples. The AV block detection criteria may be programmable and may depend at least in part on an individual patient's conduction history.

AV block detection criteria are not met when R-wave sensed event signals are received by control circuit 206 at a rate greater than the asynchronous ventricular base pacing rate such that the frequency of ventricular pacing pulses required to detect AV block is not reached. As long as AV block detection criteria are not met at block 316, control circuit 206 continues operating in the asynchronous pacing mode at block 314. Control circuit 206 may remain in the asynchronous pacing mode until AV block detection criteria are met. Ventricular pacing pulses may be delivered occasionally at the asynchronous base pacing rate as needed. If the AV block detection criteria are satisfied, e.g., if at least 2 out of four consecutive ventricular events are ventricular pacing pulses, control circuit 206 switches back to the synchronous pacing mode at block 302 to provide atrial synchronous ventricular pacing. If previously disabled, atrial event sensing from the motion sensor signal may be re-enabled upon switching from the asynchronous pacing mode back to the atrial synchronous pacing mode.

Figure 7:
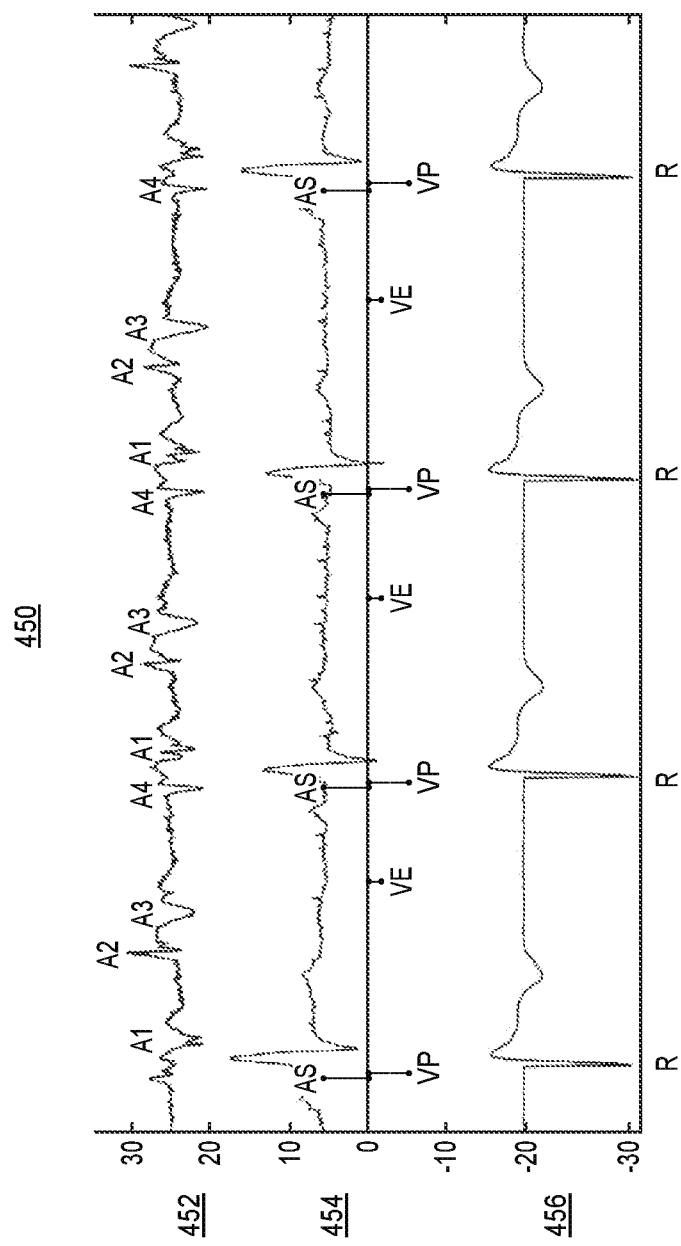
FIG. 7 is a graph of an example accelerometer signal, electrocardiogram signal with event markers and ventricular electrogram signal during an atrial synchronous ventricular pacing mode.

FIG. 7 is a graph 450 of an example accelerometer signal 452, electrocardiogram signal 454 with event markers and ventricular EGM signal 456 during an atrial synchronous pacing mode. The accelerometer signal 452 is an example of a motion signal that is received by the control circuit 206 from the motion sensor 212 (shown in FIG. 3). Accelerometer signal 452 is shown as a non-rectified signal in FIG. 7 but may be rectified by motion sensor 212 or control circuit 206 for sensing atrial (A4) events. The A1, A2, A3 and A4 events, as described in conjunction with FIG. 4, are denoted along the motion signal 452.

The "VE" markers shown along ECG signal 454 indicate the end of the A3 window, e.g., corresponding to ending time 422 shown in FIG. 5. The "AS" markers indicate the time of an atrial sensed event, e.g., when the A4 signals of accelerometer signal 452 cross the A4 sensing threshold amplitude. The "VP" markers indicate a ventricular pacing pulse delivered upon expiration of an AV interval set upon sensing the atrial events. Pacing-evoked R-waves (labeled "R") are observed on EGM signal 456. The signals 452, 454 and 456 represent appropriate atrial synchronous ventricular pacing, e.g., during a VDD pacing mode, which may be used to control single chamber ventricular pacing during AV conduction block.

Figure 8:
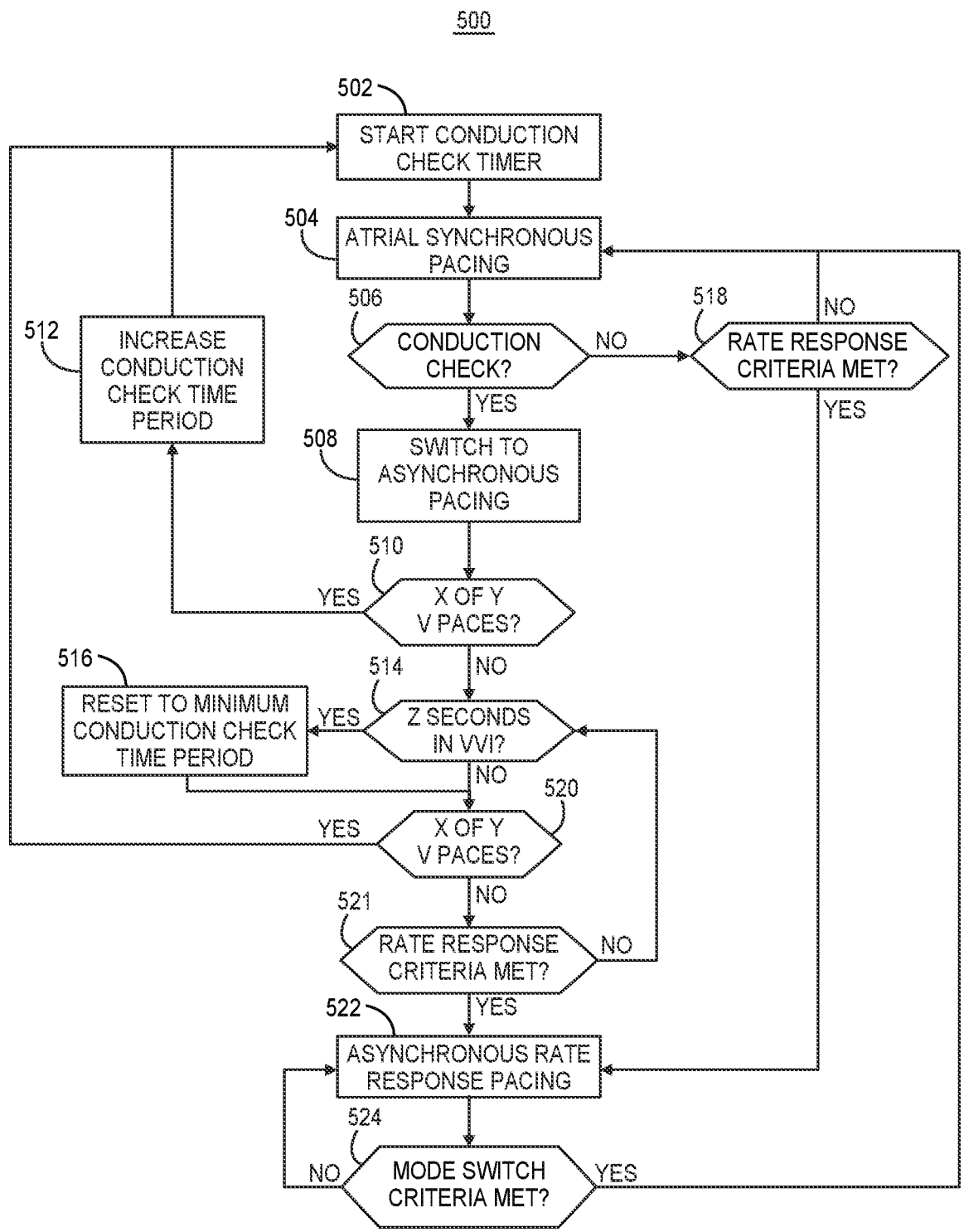
FIG. 8 is a flow chart of a method performed by the pacemaker of FIG. 1 for controlling single chamber ventricular pacing to promote AV conduction and to provide atrial synchronous ventricular pacing during periods of AV block according to another example.

FIG. 8 is a flow chart 500 of a method for controlling single chamber ventricular pacing modes to promote AV conduction and to provide atrial synchronous ventricular pacing during periods of AV block according to another example. The control circuit 206 starts a conduction check timer at block 502. Initially, the conduction check timer may be set to a relatively short time period, e.g., one minute. At block 504, pacemaker 14 operates in the atrial synchronous pacing mode by sensing atrial events, e.g., from the signal received from motion sensor 212 as described above, and delivering ventricular pacing pulses at an AV pacing interval following each sensed atrial event.

Control circuit 206 may determine whether the conduction check timer has expired at block 506. If conduction check criteria are not met at block 506 during the atrial synchronous pacing mode, e.g., the conduction check timer is still running and/or other criteria remain unmet as described below, control circuit 206 may determine if rate response criteria are met at block 518. Control circuit 206 may determine the patient activity metric from the motion signal at block 518 for determining if the rate response criteria are met. Examples of rate response criteria that may be applied at block 518 are given below in conjunction with block 521. If rate response criteria are met, control circuit 206 may switch to a rate responsive asynchronous ventricular pacing mode (e.g., VVIR or VDIR) at block 522 to provide asynchronous ventricular pacing at a SIR determined based on the patient activity metric to support the patient during increased physical activity. The VV pacing interval may initially be set to match the actual ventricular rate to avoid an abrupt change in ventricular rate upon switching to the rate responsive asynchronous pacing mode. For instance, control circuit 206 may determine an actual ventricular rate interval as the mean or median Vpace-to-Vpace interval (or RR interval) from a predetermined number of most recent ventricular cycles and set the initial VV pacing interval to the actual ventricular rate interval. The VV pacing interval may be adjusted from this initial VV pacing interval to a target heart rate interval according to the SIR to provide rate responsive pacing at block 522.

The conduction check timer started at block 502 may expire during the atrial synchronous pacing mode or during the rate responsive, asynchronous pacing mode. The conduction check is initiated by switching to a non-rate response asynchronous ventricular pacing mode. Therefore, if the conduction check timer expires during the rate response pacing mode, the conduction check is delayed until rate responsive pacing is no longer needed and control circuit 206 has switched back to the atrial synchronous pacing mode. As such, during the rate response asynchronous ventricular pacing mode at block 522, control circuit 206 determines if mode switch criteria are met at block 524. Examples of the mode switch criteria that may be applied at block 524 are described below but generally require a decrease in the patient activity metric, target heart rate, and/or SIR to below a threshold level indicating that rate responsive pacing is no longer required to support the patient's metabolic demand. When the mode switch criteria are met at block 524, control circuit 206 switches from the rate response asynchronous ventricular pacing mode back to the atrial synchronous pacing mode at block 504.

When the conduction timer expires (or has already expired), indicating it is time for a conduction check as determined at block 506, control circuit 206 may switch from the atrial synchronous pacing mode to the asynchronous ventricular pacing mode at block 508. Atrial event sensing may be disabled or ignored during the asynchronous pacing mode. Only ventricular events may be used to determine if AV conduction is present or if AV block is detected.

In some examples, the switch to the asynchronous pacing mode at block 508 occurs only when the conduction check timer is expired and other conduction check criteria are satisfied. For instance, the patient activity metric, target heart rate or SIR may be required to be less than a threshold. The patient activity metric, target heart rate and/or SIR may be determined during the atrial synchronous pacing mode even though it is not used by pacemaker 14 for controlling the ventricular pacing rate. The SIR may be compared to the programmed lower pacing rate plus an increment rate during atrial synchronous pacing. The programmed lower pacing rate may range from 30 pulses per minute to 60 pulses per minute and the predetermined increment may be 5 to 10 pulses per minute, as examples. If the SIR is not less than or equal to the programmed base pacing rate plus the increment at the time that the conduction check timer expires, the control circuit 206 may wait for the SIR to fall to less than or equal to the threshold rate.

In other examples, conduction check criteria required at block 506 may include sensing at least one ventricular event following a sensed atrial event while in the atrial synchronous pacing mode. For instance, if the conduction check timer has expired (and the patient activity metric, target heart rate and/or SIR are less than a threshold), control circuit 206 may extend the AV pacing interval for one or more cardiac cycles to determine if an intrinsic R-wave sensed event signal is received from sensing circuit 204 before the extended AV pacing interval expires. The AV pacing interval may be extended from 10 ms to 100 ms, 150 ms, 200 ms or more to determine if an intrinsic R-wave follows the sensed atrial event within an expected AV conduction time, indicating AV conduction may be intact. In another example, the ventricular pacing pulse may be withheld for one cardiac cycle to determine if an intrinsic R-wave is sensed. The ventricular pacing pulse may be withheld by setting the AV pacing interval to a maximum time interval. If AV conduction evidence is detected based on one or more sensed R-waves during the atrial synchronous pacing mode, the switch to the asynchronous pacing mode is made at block 508. If an R-wave is not sensed during the extended AV interval, the control circuit 206 may remain in the atrial synchronous pacing mode in some examples.

At block 510, control circuit 206 determines if AV block detection criteria are satisfied during the asynchronous pacing mode. The base pacing rate during the asynchronous pacing mode may be set to a minimum or relatively low base pacing rate, e.g., 30, 40, or 50 pulses per minute. In other examples, the base pacing rate may be set relatively higher, e.g., 60 pulses per minute, and may be decreased at predetermined time intervals during the asynchronous pacing mode to determine if AV conduction block criteria are satisfied at block 510. In one example if X out of Y ventricular events are ventricular pacing pulses during the asynchronous pacing mode, e.g., if at least two out of four ventricular events are ventricular pacing pulses, AV conduction block is detected, and control circuit 206 switches back to the atrial synchronous pacing mode (return to block 502). In this example, if two consecutive ventricular pacing pulses or if two pacing pulses are delivered separated by one sensed R-wave, the X of Y criteria may be determined to be met without having to wait for a fourth ventricular event to occur.

When AV block is detected at block 510 relatively early after switching to the asynchronous pacing mode, control circuit 206 may increase the conduction check time period at block 512. For instance, the conduction check time period may be doubled from the previous conduction check time period. If the timer is initially set to one minute at block 502, the timer may be set to two minutes at block 512 and restarted at block 502 upon switching back to the atrial synchronous pacing mode at block 504 responsive to detecting AV block. Each time AV conduction block is detected relatively early after switching to the asynchronous pacing mode, resulting in control circuit 206 switching back to the atrial synchronous pacing mode, the conduction check time period may be increased, e.g., doubled, up to a maximum conduction check time period. In this way, frequent conduction checks and pacing mode switching is avoided if AV block is detected within a predetermined time period or number of ventricular events after switching to the asynchronous pacing mode, e.g., within one minute or less or within 30 ventricular events or less. In one example, the conduction check time period is doubled each time AV conduction block is detected within the first 20 seconds or the first 20 ventricular events after switching to the asynchronous pacing mode.

In other examples, the conduction check time period is increased, e.g., doubled, each time control circuit 206 switches to the asynchronous ventricular pacing mode from the atrial synchronous ventricular pacing mode in response to the conduction check timer expiring. When AV block is detected within a threshold number of ventricular cycles, e.g., 20 cycles, in the asynchronous ventricular pacing mode (or within a specified time interval), the conduction check timer remains at the increased setting upon switching back to the atrial synchronous ventricular pacing mode. When AV block is detected after the threshold number of ventricular cycles, the conduction check time period is reset to the minimum conduction check time period, e.g., 1 minute, upon switching back to the atrial synchronous ventricular pacing mode. The conduction check timer may be increased, e.g., doubled, each time control circuit 206 switches to the asynchronous pacing mode up to a maximum conduction check time period, after which the conduction check time period is no longer increased unless reset again to the minimum time period. The maximum conduction check time period may be 12 hours, 16 hours, 20 hours, or 24 hours or longer, as examples.

If the threshold number of X of Y ventricular events being ventricular pacing pulses is not reached at block 510, and a predetermined time interval (e.g., 20 seconds) or a predetermined number of ventricular events (e.g., 20 ventricular events) has been reached ("yes" branch of block 514), the conduction check time period may be reset back to the minimum time period, e.g., one minute, at block 516. When the AV block detection criteria are not satisfied relatively early during the asynchronous pacing mode, e.g., during the first 20 seconds or first 20 ventricular events (or other predetermined interval), indicating AV conduction is occurring, more frequent AV conduction checks are warranted upon switching back to the atrial synchronous pacing mode to promote AV conduction along intrinsic conduction pathways and minimize ventricular pacing. When X ventricular paces out of Y ventricular events are detected after the conduction check time period is reset to a minimum ("yes" branch of block 520), control circuit 206 switches back to atrial synchronous ventricular pacing by returning to block 502. The conduction check timer is restarted at the minimum conduction check time period, and atrial synchronous pacing resumes at block 504.

As long as the criteria of X ventricular paces out of Y ventricular events (or other AV block detection criteria) are not satisfied ("no" branch of block 520), AV block is not detected, and control circuit 206 remains in the asynchronous pacing mode with a base pacing rate set to a relatively low rate, e.g., 40 pulses per minute, to promote AV conduction along intrinsic conduction pathways. During the asynchronous pacing mode, control circuit 206 may determine a patient activity metric from the motion signal received from motion sensor 212. The patient activity metric is used to determine a target heart rate and SIR for determining if rate responsive pacing is needed due to an increase in patient activity. The patient activity metric, target heart rate, and/or SIR may be compared to rate response switching criteria at block 521. In one example, the rate response switching criteria applied at block 521 (and at block 518) requires that a pacing rate determined based on patient activity be greater than the ADL rate and greater than the actual ventricular rate plus a rate increment for a predetermined minimum time interval, e.g., at least 10 seconds. The pacing rate determined based on patient activity may be the target heart rate. In other examples, the SIR determined from the target heart rate, e.g., by applying a transfer function to the target heart rate, may be compared to the rate response switching criteria. The rate increment added to the actual ventricular rate may be 20 or 30 pulses per minute as examples. The actual ventricular rate may be determined as the rate corresponding to a median RR interval (RRI). Each RRI is determined by control circuit 206 as the time interval between two consecutive R-wave sensed event signals received from sensing circuit 204. The median RRI is determined from a predetermined number of RRIs, e.g., from ten RRIs. In some examples, paced ventricular intervals may be included in the RRIs used for determining the median RRI at block 521 in cases where ventricular paces are delivered but less frequently than the X of Y criteria for detecting AV block.

If the patient activity metric, target heart rate or corresponding SIR does not satisfy rate response criteria at block 521 ("no" branch), control circuit 206 continues to operate in the asynchronous pacing mode and monitors for AV block based on the criteria of X of Y ventricular events being ventricular pacing pulses at block 520. Control circuit 206 may return to block 514 to determine if Z seconds (or a predetermined number of ventricular cycles) has elapsed since entering the asynchronous pacing mode. It is recognized that once Z seconds (or a predetermined number of ventricular cycles) have elapsed after switching to the asynchronous pacing mode and the conduction time period has been reset back to the minimum time period at block 516, control circuit 206 does not need to repeat the operations at blocks 514 and 516 again while still in the asynchronous pacing mode.

If the rate response criteria are satisfied at block 521, control circuit 206 switches to a rate responsive asynchronous ventricular pacing mode, e.g., VVIR or VDIR pacing mode, at block 522. In one example, if the target heart rate determined from the patient activity metric is more than the ADL rate and more than 20 pulses per minute (or other predetermined rate increment) greater than the actual ventricular rate (which may be determined as the median RRI), control circuit 206 switches to a rate responsive asynchronous ventricular pacing mode, e.g., VVIR or VDIR, at block 522 to provide ventricular rate support during patient activity. In order to avoid an abrupt change in ventricular rate, control circuit 206 may set the VV pacing interval to the actual ventricular rate, e.g., a most recently determined average or median RRI, upon switching to the rate responsive asynchronous pacing mode. The SIR may then be adjusted up to the target heart rate according to a transfer function to gradually adjust the pacing rate to the target heart rate based on patient physical activity.

During the rate responsive asynchronous pacing mode at block 522, control circuit 206 continues to determine the SIR based on a patient activity metric and corresponding target heart rate determined from the motion signal. The pacing rate is controlled according to the SIR, and the patient activity metric, target heart rate and/or SIR may be compared to pacing mode switching criteria at block 524. Control circuit 206 may monitor the patient activity metric, the target heart rate and/or SIR to determine when the patient's activity level has decreased to a point that rate responsive pacing is no longer needed. As long as the target heart rate and/or SIR remain greater than a rate threshold ("no" branch of block 524), control circuit 206 remains in the asynchronous pacing mode (block 522). In one example, the rate threshold is the ADL rate though other rate thresholds may be defined for comparison to the target heart rate and to the SIR. In an illustrative example, the mode switching criteria may be met at block 524 when the target heart rate is less than the ADL rate for at least ten seconds (or other predetermined time period or number of ventricular cycles) and the SIR is less than the ADL rate. When the mode switch criteria are met at block 524, control circuit 206 switches back to the atrial synchronous pacing mode at block 504, with atrial event sensing re-enabled (if previously disabled). In order to avoid abrupt changes in ventricular rate upon switching back to the atrial synchronous pacing mode from the rate responsive asynchronous pacing mode, the VV pacing interval may be gradually increased from the last SIR interval until atrial synchronous ventricular pacing takes over in the atrial synchronous pacing mode.

The conduction check timer may still be running upon switching back to the atrial synchronous pacing mode or may have expired while operating in the rate response pacing mode at block 522. If the conduction check timer has expired, and other AV conduction check criteria are satisfied at block 506 (as described above), control circuit 206 may switch to the asynchronous pacing mode at block 508 to monitor for ventricular pacing frequency as evidence of AV block at block 510. If the conduction check timer is still running, control circuit 206 continues to operate in the atrial synchronous pacing mode until the timer expires.

Figure 9:
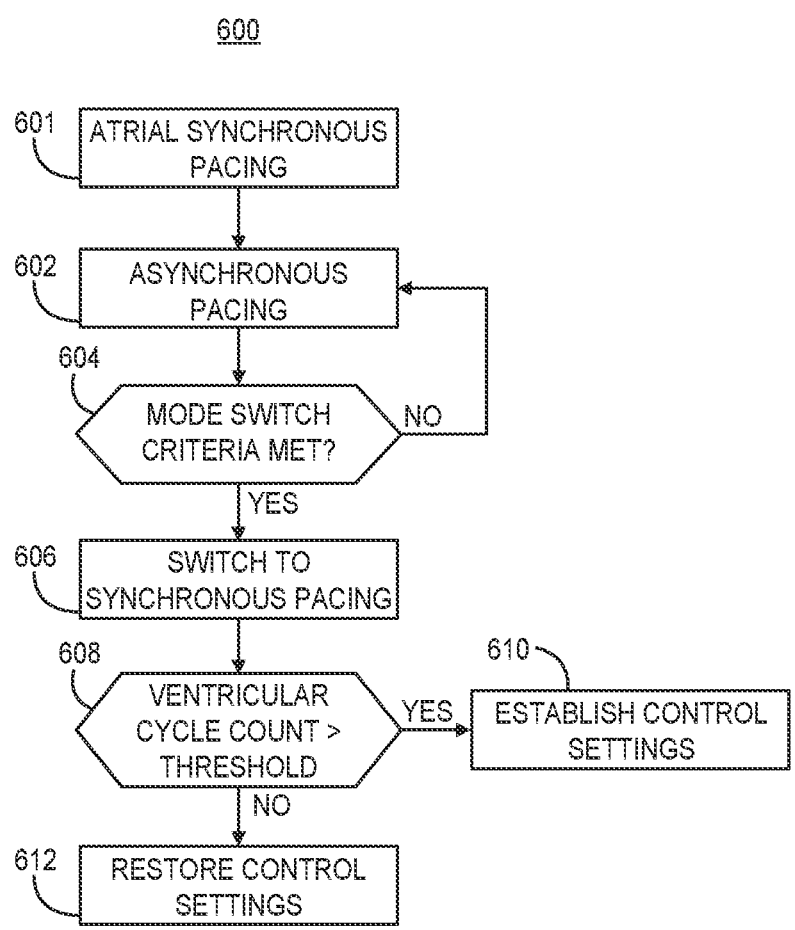
FIG. 9 is a flow chart of a method for switching from an asynchronous pacing mode back to the atrial synchronous pacing mode according to some examples.

FIG. 9 is a flow chart 600 of a method for switching from an asynchronous pacing mode back to the atrial synchronous pacing mode according to some examples. Control circuit 206 may switch from the atrial synchronous pacing mode (block 601) to an asynchronous pacing mode (block 602) upon expiration of a conduction check timer as described above. At other times, control circuit 206 may switch from the atrial synchronous pacing mode (block 601) to an asynchronous rate responsive pacing mode when ventricular rate support is needed based on rate response criteria being met as described in conjunction with FIG. 8. Accordingly, the asynchronous pacing mode at block 602 may be a rate responsive mode, e.g., VVIR, or a non-rate responsive mode, e.g., VVI, with a lower base pacing rate of 40 pulses per minute (or other base pacing rate). When control circuit 206 switches from the atrial synchronous to the asynchronous pacing mode, one or more adjustable control parameters may be buffered in memory 210. During the atrial synchronous pacing mode, one or more auto-adjusting control parameters may be used in controlling A4 event sensing from the motion sensor signal and/or scheduling ventricular pacing pulses.

For example, the A3 window ending time 422, the first value 446 of the A4 threshold amplitude 444 during the A3 window and the second value 448 of the A4 threshold amplitude 444 after the A3 window ending time may be automatically adjusted by control circuit 206 during the atrial synchronous pacing mode. For instance, the A3 window ending time 422 may be set based on a percentage of the ventricular cycle length (or an average, median or other metric of multiple ventricular cycle lengths). The first value 446 of the A4 threshold amplitude 444 may be set based on the motion sensor signal peak amplitude determined during one or more the A3 windows 424 and/or the motion sensor peak amplitude after the end the A3 window. The second value 448 of the A4 threshold amplitude 444 may be adjustable based on the maximum peak amplitude of the motion sensor signal after the A3 window, which may be associated with one or more sensed A4 events. The latest values of the A3 window ending time 422, the first value 446 and the second value 448 of the A4 threshold amplitude may be buffered in memory 210 upon switching from the atrial synchronous pacing mode to the asynchronous pacing mode at block 602.

As described above, control circuit 206 may adjust a rate smoothing interval based on one or more actual ventricular cycle lengths. For example, the rate smoothing interval may be set to be within 100 to 150 ms of one or more of the most recent actual ventricular cycle lengths to avoid an abrupt change in ventricular rate when an A4 event is not sensed. For instance, the rate smoothing interval may be set to a running average, median or other metric of one or more recent ventricular cycle lengths plus an increment of 100 to 150 milliseconds. In the absence of a sensed A4 event, a ventricular pacing pulse is delivered at a VV pacing interval set to the rate smoothing interval. The latest value of the rate smoothing interval may be buffered in memory 210 upon switching to the asynchronous pacing mode at block 602.

While control circuit 206 is operating in the asynchronous pacing mode, at block 602, a counter or timer included in control circuit 206 may track the total number of ventricular cycles, the total number of ventricular pacing pulses delivered, and/or the total time since switching to the asynchronous pacing mode. The total number of ventricular cycles, including paced and sensed ventricular cycles (when an intrinsic R-wave is sensed before the VV pacing interval expires), may be counted during the asynchronous pacing mode.

At block 604, control circuit 206 determines when mode switch criteria are met for switching back to the atrial synchronous pacing mode. The mode switch criteria may be met at block 604 when AV conduction block is detected as described above. For example, when two ventricular pacing pulses are delivered out of four consecutive ventricular cycles. Other criteria, also described above, may also be required at block 604 in order to switch back to the atrial synchronous pacing mode, such as the patient activity metric, SIR and/or target rate being less than respective thresholds for a predetermined time interval.

When the mode switch criteria are met, control circuit 206 switches back to the atrial synchronous pacing mode at block 606. Control circuit 206 checks the ventricular cycle counter at block 608 to determine if the asynchronous pacing mode was in effect for more than a threshold number of ventricular cycles. The threshold number of ventricular cycles may be 10 cycles, 20 cycles, 30 cycles, or 40 cycles, as examples. In other examples, control circuit 206 may compare a total number of ventricular pacing pulses, total number of sensed R-waves, and/or a total time of operation in the asynchronous pacing mode to respective thresholds at block 608. A threshold time interval, for instance, may be 20 seconds, 30 seconds, one minute, five minutes or other selected time interval.

When the asynchronous pacing mode is in effect less than or equal to a threshold number of ventricular cycles, (or threshold time interval) the latest values buffered in memory 210 for one or more adjustable control parameters used by control circuit 206 during the atrial synchronous pacing mode may be restored at block 612 upon switching back to the atrial synchronous pacing mode. For instance, when the asynchronous pacing mode is in effect for 20 ventricular cycles or less, a previous value or setting of at least one control parameter that was in effect at the time that the pacing mode switched from the atrial synchronous pacing mode to the asynchronous pacing mode may be restored and continue to be used upon switching back to the atrial synchronous pacing mode.

Among the control parameters that may be restored at block 612 may be the rate smoothing interval, the A3 window ending time, the first, higher value of the A4 threshold amplitude applied during the A3 window and/or the second, lower value of the A4 threshold amplitude applied after the A3 window. The most recently stored values of these control parameters, e.g., at the time of switching from the atrial synchronous pacing mode to the asynchronous pacing mode, may be restored at block 612. The control parameter values may be retrieved from memory 210 by control circuit 206.

When the asynchronous pacing mode is in effect for more than 20 ventricular cycles (or other selected cycle number threshold or time threshold) at block 608, control circuit 210 may establish new starting values for one or more control parameters at block 610 upon switching back to the atrial synchronous pacing mode. In one example, the rate smoothing interval is set to the currently programmed base pacing rate interval at block 610. At the end of the previous atrial synchronous ventricular pacing mode, the rate smoothing interval may be at a value based on one or more actual ventricular cycle lengths. This rate smoothing interval may be restored when switching back to the atrial synchronous pacing mode within a threshold number of ventricular cycle lengths (block 612). After the threshold number of ventricular cycle lengths in the asynchronous pacing mode, however, the rate smoothing interval may be reset based on the programmed lower ventricular pacing rate, e.g., to an interval of 1000 milliseconds if the lower ventricular pacing rate is programmed to 60 pulses per minute during the atrial synchronous pacing mode. The rate smoothing interval may be adjusted from the lower ventricular pacing rate interval as needed based on actual ventricular cycle lengths determined by control circuit 206 during the atrial synchronized pacing mode. In other examples, the starting value of the rate smoothing interval set at block 610 may be based one or more of the most recent ventricular cycle lengths ending the asynchronous pacing mode. For example, the rate smoothing interval may be set to the last ventricular cycle of the asynchronous pacing mode or to the last ventricular cycle of the asynchronous pacing mode plus an increment. In still other examples, the rate smoothing interval may be set based on a patient physical activity level or metric or the SIR determined based on the motion signal or another signal correlated to patient physical activity level.

In another example, at block 610, a starting value of the A3 window ending time may be established upon switching back to the atrial synchronous pacing mode after the ventricular cycle count exceeds the threshold at block 608. The A3 window ending time may be set to a percentage of the last paced ventricular cycle that ended the asynchronous pacing mode, as an example. The A3 window ending time may be updated after switching to the atrial synchronous pacing mode based on actual ventricular cycle lengths determined by control circuit 206, e.g., a percentage of a mean or median ventricular cycle length determined from a specified number of ventricular cycles. In other examples, the initial A3 window ending time may be set to a fixed interval from the ending asynchronous ventricular pacing pulse upon switching back to the atrial synchronous pacing mode.

In still other examples, the starting first and/or second values of the A4 threshold amplitude may be established at block 610 when the asynchronous pacing mode has been in effect for greater than the threshold number of ventricular cycles at block 608. In one example, the first value 446 of the A4 threshold amplitude 446 (during the A3 window 424) may be set initially to a maximum upper limit, e.g., to 255 ADC units or about 25.5 m/s$^2$. The second lower A4 threshold amplitude value 448 (applied after the A3 window ending time 422 shown in FIG. 5) may be set to the most recently buffered second value of the A4 threshold amplitude, at the end of the previous atrial synchronous pacing mode, plus an offset. The buffered second value of the A4 threshold amplitude may range from 0.5 m/s$^2$ to 5.0 m/s$^2$, for instance. The offset added to the buffered second value may be 0.1 to 1.0 m/s$^2$ and is 0.3 m/s$^2$ in one example. To illustrate, if the buffered second value of the A4 threshold amplitude is 2.0 m/s$^2$, the starting value may be established at block 610 as 2.3 m/s$^2$. The starting, second A4 threshold amplitude value may be limited to a maximum possible value, e.g., corresponding to a maximum range of an ADC of motion sensor 212. When adding the offset to the buffered value causes the second A4 threshold amplitude value to exceed the maximum limit, the starting second A4 threshold amplitude value may be set to the maximum limit at block 610.

In some examples, the first A4 threshold amplitude value may be established at block 610 based on the established second A4 threshold amplitude value. For instance, the first A4 threshold amplitude value may be set to a multiple of the second A4 threshold amplitude value. In other examples, the first A4 threshold amplitude value may be established after switching back to the atrial synchronous pacing mode by determining a maximum peak amplitude (A3 event amplitude) during a predetermined number of A3 windows. For instance, the first A4 threshold amplitude value (during the A3 windows) may be held at its maximum upper limit, e.g., 255 ADC units, for a predetermined number of ventricular cycles after switching back to the atrial synchronous pacing mode, e.g., for the first 8 ventricular cycles after switching back to the atrial synchronous pacing mode. Control circuit 206 may determine the peak amplitude of the motion sensor signal as the A3 event amplitude during each of the A3 windows for each one of the predetermined number of ventricular cycles. The median of the predetermined number of A3 event amplitudes may be used to adjust the first A4 threshold amplitude value from the maximum upper limit after the predetermined number of ventricular cycles. For example, the first A4 threshold amplitude value may be set to a multiple of the median A3 event amplitude or to the median A3 event amplitude plus an offset.

In still other examples, the first value of the A4 sensing threshold amplitude may be set based on a combination of the second A4 threshold amplitude value established at block 610 and one or more A3 event amplitudes determined after switching back to the atrial synchronous pacing mode. For instance, the first A4 sensing threshold amplitude value may be set to the second A4 sensing threshold amplitude value established at block 610 plus the product of the median A3 event amplitude (determined from a specified number of A3 windows) multiplied by a predetermined factor, e.g., a factor of 1.5 to 2. In some examples, an offset, e.g., 0 to 0.5 m/s$^2$, may be added to the sum of the second A4 threshold amplitude value and the product of the median A3 event amplitude and the predetermined factor.

It is recognized that numerous variations may be conceived for establishing a starting value of one or more auto-adjusting control parameters used for sensing cardiac events and/or scheduling ventricular pacing pulses upon switching back to the atrial synchronous pacing rate when the asynchronous pacing mode has been in effect for greater than a threshold number of ventricular cycles (or threshold time interval). Furthermore, it is to be understood that a different threshold number of ventricular cycles may be applied to different control parameters for determining when to restore a buffered value of a control parameter vs. establishing a new, starting value of a control parameter. For example, a new rate smoothing interval may be established when the ventricular cycle count is greater than a first threshold, and new A4 sensing control parameters may be established when the ventricular cycle count is greater than a second threshold, different than the first threshold. When the asynchronous pacing mode is in effect for less than (or equal to) the first threshold number of ventricular cycles, all buffered values of control parameters may be restored at block 612. When the asynchronous pacing mode is in effect for more than the first threshold number of ventricular cycles, the buffered rate smoothing interval may be discarded, and a new rate smoothing interval may be established at block 610. The A4 sensing control parameters, however, e.g., the A3 window ending time and A4 threshold amplitude values, may be restored to the most recently buffered values at block 612 when the ventricular cycle count is greater than a first threshold but less than or equal to a second threshold number of ventricular cycles. When the asynchronous pacing mode is in effect for more than the second threshold number of ventricular cycles, the buffered values of auto-adjusting control parameters, including the rate smoothing interval and the A4 sensing control parameters, may be discarded and new starting values may be established at block 610.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a pacemaker has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:
1. A pacemaker comprising:
a pulse generator configured to generate ventricular pacing pulses; and
a control circuit configured to:
  receive a signal from a sensor;
  start a conduction check time interval;
  operate in an atrial synchronous ventricular pacing mode by:
    identifying atrial event signals from the signal; and
    controlling the pulse generator to generate ventricular pacing pulses synchronized to the identified atrial event signals;
  detect an expiration of the conduction check time interval;
  responsive to the conduction check time interval expiring, initiate a conduction check by switching from operating in the atrial synchronous ventricular pacing mode to operating in an asynchronous ventricular pacing mode;
  after switching to the asynchronous ventricular pacing mode upon expiration of the conduction check time interval, determine that atrioventricular block criteria are met during the asynchronous ventricular pacing mode; and
  responsive to determining that atrioventricular block criteria are met, switch back to operating in the atrial synchronous ventricular pacing mode.
2. The pacemaker of claim 1, wherein the control circuit is configured to determine that atrioventricular block detection criteria are satisfied by:
  identifying a plurality of ventricular events; and determining that the plurality of ventricular events includes a threshold number of ventricular pacing pulses generated by the pulse generator.

3. The pacemaker of claim 1, further comprising the sensor configured to sense the signal.

4. The pacemaker of claim 3, wherein:
the sensor comprises a motion sensor configured to sense the signal as a motion signal; and
the control circuit is configured to identify the atrial event signals from the motion signal during the atrial synchronous ventricular pacing mode.

5. The pacemaker of claim 1, wherein the control circuit is further configured to:
determine that the atrioventricular block detection criteria are satisfied within a predetermined number of ventricular cycles after switching to the asynchronous ventricular pacing mode;
increase the conduction check time interval in response to the atrioventricular block detection criteria being satisfied within the predetermined number of ventricular cycles; and
start the increased conduction check time interval upon switching back to operating in the atrial synchronous ventricular pacing mode.

6. The pacemaker of claim 5, wherein the control circuit is further configured to:
increase the conduction check time interval by doubling the conduction check time interval;
switch to the asynchronous ventricular pacing mode after the increased conduction check time interval expires; and
double the conduction check time interval each time the atrioventricular block detection criteria are satisfied within the predetermined number of ventricular cycles after switching to the asynchronous ventricular pacing mode, the conduction check time interval being doubled up to a maximum conduction check time interval.

7. The pacemaker of claim 1, wherein the control circuit is further configured to:
determine that the atrioventricular block detection criteria are satisfied after operating in the asynchronous ventricular pacing mode for at least a predetermined number of ventricular cycles; and
adjust the conduction check time interval to a minimum time interval in response to the atrioventricular block detection criteria being satisfied after operating in the asynchronous ventricular pacing mode for at least the predetermined number of ventricular cycles.

8. The pacemaker of claim 1, wherein the control circuit is further configured to:
detect a first patient physical activity level;
determine a first pacing rate based on the first patient physical activity level;
determine that the first pacing rate meets rate response criteria;
control the pulse generator to deliver ventricular pacing pulses in a rate responsive, asynchronous ventricular pacing mode in response to the first pacing rate meeting the rate response criteria;
detect the expiration of the conduction check time interval during the asynchronous ventricular pacing mode;
detect a second patient physical activity level;
determine a second pacing rate based on the second patient physical activity level;
determine that the second pacing rate does not meet the rate response criteria; and switch to operating in the asynchronous ventricular pacing mode in response to the conduction check time interval being expired and the second pacing rate not meeting the rate response criteria.

9. The pacemaker of claim 1, wherein the control circuit is further configured to operate in the asynchronous ventricular pacing mode by:
setting a ventricular pacing interval to a base pacing rate interval; and
generating a ventricular pacing pulse upon expiration of the ventricular pacing interval.

10. The pacemaker of claim 1, wherein the control circuit is further configured to:
extend an atrial-ventricular pacing interval in response to the conduction check time interval expiring;
sense an intrinsic R-wave by the cardiac electrical sensing circuit during the extended atrial-ventricular pacing interval; and
switch to the asynchronous ventricular pacing mode in response to the conduction check time interval being expired and the intrinsic R-wave being sensed during the extended atrial-ventricular pacing interval.

11. The pacemaker of claim 1, wherein the control circuit is further configured to:
determine that the asynchronous ventricular pacing mode is in effect for greater than one of a threshold number of ventricular cycles or a threshold time interval; and
establish a starting value of at least one control parameter upon switching back to operating in the atrial synchronous ventricular pacing mode.

12. A method performed by a medical device, the method comprising:
starting a conduction check time interval;
operating in an atrial synchronous ventricular pacing mode by:
receiving a signal from a sensor;
identifying atrial event signals from the signal; and
controlling a pulse generator to generate ventricular pacing pulses synchronized to the identified atrial event signals;
detecting an expiration of the conduction check time interval;
responsive to the conduction check time interval expiring, initiating a conduction check by switching from operating in the atrial synchronous ventricular pacing mode to operating in an asynchronous ventricular pacing mode;
after switching to the asynchronous ventricular pacing mode upon expiration of the conduction check time interval, determining that atrioventricular block criteria are met during the asynchronous ventricular pacing mode; and
responsive to determining that atrioventricular block criteria are met, switching back to operating in the atrial synchronous ventricular pacing mode.

13. The method of claim 12, wherein determining that atrioventricular block detection criteria are satisfied comprises:
identifying a plurality of ventricular events; and
determining that the plurality of ventricular events includes a threshold number of delivered ventricular pacing pulses.

14. The method of claim 12, further comprising:
receiving the signal from the sensor by receiving a motion signal from a motion sensor; and
identifying the atrial event signals from the motion signal during the atrial synchronous ventricular pacing mode.

15. The method of claim 12, further comprising:
determining that the atrioventricular block detection criteria are satisfied within a predetermined number of ventricular cycles after switching to the asynchronous ventricular pacing mode;
increasing the conduction check time interval in response to the atrioventricular block detection criteria being satisfied within the predetermined number of ventricular cycles; and
starting the increased conduction check time interval upon switching back to operating in the atrial synchronous ventricular pacing mode.

16. The method of claim 15, further comprising:
increasing the conduction check time interval by doubling the conduction check time interval;
switching to the asynchronous ventricular pacing mode after the increased conduction check time interval expires; and
doubling the conduction check time interval each time the atrioventricular block detection criteria are satisfied within the predetermined number of ventricular cycles after switching to the asynchronous ventricular pacing mode, the conduction check time interval being doubled up to a maximum conduction check time interval.

17. The method of claim 12, further comprising:
determining that the atrioventricular block detection criteria are satisfied after operating in the asynchronous ventricular pacing mode for at least a predetermined number of ventricular cycles; and
adjusting the conduction check time interval to a minimum time interval in response to the atrioventricular block detection criteria being satisfied after operating in the asynchronous ventricular pacing mode for at least the predetermined number of ventricular cycles.

18. The method of claim 12, further comprising:
detecting a first patient physical activity level;
determining a first pacing rate based on the first patient physical activity level;
determining that the first pacing rate meets rate response criteria;
delivering ventricular pacing pulses in a rate responsive, asynchronous ventricular pacing mode in response to the first pacing rate meeting the rate response criteria;
detecting the expiration of the conduction check time interval during the asynchronous ventricular pacing mode;
detecting a second patient physical activity level;
determining a second pacing rate based on the second patient physical activity level;
determining that the second pacing rate does not meet the rate response criteria; and
switching to operating in the asynchronous ventricular pacing mode in response to the conduction check time interval being expired and the second pacing rate not meeting the rate response criteria.

19. The method of claim 12, wherein operating in the asynchronous ventricular pacing mode comprises:
setting a ventricular pacing interval to a base pacing rate interval; and
generating a ventricular pacing pulse upon expiration of the ventricular pacing interval.

20. The method of claim 12, further comprising:
extending an atrial-ventricular pacing interval in response to the conduction check time interval expiring;
sensing an intrinsic R-wave by the cardiac electrical sensing circuit during the extended atrial-ventricular pacing interval; and
switching to the asynchronous ventricular pacing mode in response to the conduction check time interval being expired and the intrinsic R-wave being sensed during the extended atrial-ventricular pacing interval.

21. The method of claim 12, further comprising:
determining that the asynchronous ventricular pacing mode is in effect for greater than one of a threshold number of ventricular cycles or a threshold time interval; and
establishing a starting value of at least one control parameter upon switching back to operating in the atrial synchronous ventricular pacing mode.

22. A non-transitory, computer-readable storage medium comprising a set of instructions which, when executed by a control circuit of a pacemaker, cause the pacemaker to:
start a conduction check time interval;
operate in an atrial synchronous ventricular pacing mode by:
receiving a signal from a sensor;
identifying atrial event signals from the signal; and
controlling a pulse generator to generate ventricular pacing pulses synchronized to the identified atrial event signals;
detect an expiration of the conduction check time interval;
responsive to the conduction check time interval expiring, initiate a conduction check by switching from operating in the atrial synchronous ventricular pacing mode to operating in an asynchronous ventricular pacing mode;
after switching to the asynchronous ventricular pacing mode upon expiration of the conduction check time interval, determine that atrioventricular block criteria are met during the asynchronous ventricular pacing mode; and
responsive to determining that atrioventricular block criteria are met, switch back to operating in the atrial synchronous ventricular pacing mode.

* * * * *